US009284568B2

(12) United States Patent
Saphire

(10) Patent No.: US 9,284,568 B2
(45) Date of Patent: Mar. 15, 2016

(54) METHODS FOR TRANSFORMING EUKARYOTIC ALGAE

(75) Inventor: Andrew C. S. Saphire, Solana Beach, CA (US)

(73) Assignee: Tabletop Energy, Tiburon, CA (US)

( * ) Notice: Subject to any disclaimer, the term of this patent is extended or adjusted under 35 U.S.C. 154(b) by 810 days.

(21) Appl. No.: 12/594,767

(22) PCT Filed: Apr. 3, 2008

(86) PCT No.: PCT/US2008/059294
§ 371 (c)(1),
(2), (4) Date: May 3, 2010

(87) PCT Pub. No.: WO2008/124526
PCT Pub. Date: Oct. 16, 2008

(65) Prior Publication Data
US 2010/0279390 A1    Nov. 4, 2010

Related U.S. Application Data

(60) Provisional application No. 60/909,897, filed on Apr. 3, 2007.

(51) Int. Cl.
| C12P 7/02 | (2006.01) |
| C07H 21/04 | (2006.01) |
| C07H 21/02 | (2006.01) |
| C12N 9/04 | (2006.01) |
| C12N 9/88 | (2006.01) |
| C12N 15/00 | (2006.01) |
| C12N 1/20 | (2006.01) |
| C12N 1/12 | (2006.01) |
| C12N 15/82 | (2006.01) |
| C12P 7/04 | (2006.01) |
| C12P 7/06 | (2006.01) |
| C12P 7/16 | (2006.01) |

(52) U.S. Cl.
CPC .......... *C12N 15/8214* (2013.01); *C12N 9/0006* (2013.01); *C12N 9/88* (2013.01); *C12N 15/8201* (2013.01); *C12P 7/02* (2013.01); *C12P 7/04* (2013.01); *C12P 7/065* (2013.01); *C12P 7/16* (2013.01); *Y02E 50/10* (2013.01); *Y02E 50/17* (2013.01)

(58) Field of Classification Search
CPC .. C12N 9/0008; C12N 15/8221; C12N 9/006; C12N 15/8201; C12N 9/88; C12N 15/8214; C12P 7/065; C12P 7/02
See application file for complete search history.

(56) References Cited

U.S. PATENT DOCUMENTS

| 5,270,175 A | 12/1993 | Moll |
| 6,686,516 B2 | 2/2004 | Lebel et al. |
| 6,699,696 B2 | 3/2004 | Woods et al. |
| 7,973,214 B2 * | 7/2011 | Lee ............................. 800/284 |
| 2002/0104119 A1 * | 8/2002 | Fischer et al. ................ 800/278 |
| 2003/0087368 A1 | 5/2003 | Maupin-Furlow et al. |
| 2004/0101865 A1 | 5/2004 | Cirpus et al. |
| 2004/0231015 A1 | 11/2004 | Daniell |

FOREIGN PATENT DOCUMENTS

| WO | WO 00/00619 A2 | 1/2000 |
| WO | WO 2008/039450 A2 | 4/2008 |

OTHER PUBLICATIONS

Branden et al. Introduction to Protein Structure, Garland Publishing Inc., New York, p. 247, 1991.*
Coll, J.M., "Review. Methodologies for Transferring DNA into Eukaryotic Microalgae," Spanish Journal of Agricultural Research, Dec. 2006, pp. 316-330, vol. 4, No. 4.
Deng, M-D. et al., "Ethanol Synthesis by Genetic Engineering in Cyanobacteria," Applied and Environmental Microbiology, Feb. 1999, pp. 523-528, vol. 65, No. 2.
European Examination Report, European Application No. 08745035.9, Mar. 25, 2011, 5 pages.
Lapidot, M. et al., "Stable Choloroplast Transformation of the Unicellular Red Alga *Porphyridium* Species," Plant Physiology, American Society of Plant Physiologists, May 2002, pp. 7-12, vol. 129, No. 1.
Leon, R. et al., "Nuclear Transformation of Eukaryotic Microalgae," Advances in Experimental Medicine and Biology, Jan. 2007, pp. 1-11, vol. 16.
Matsunaga, T. et al., "Marine Microalgae," Adv Biochem Engin/Biotechnol, 2005, pp. 165-188, vol. 96.
Mayfield, S. et al., "Expression and Assembly of a Fully Active Antibody in Algae," Proceedings of the national Academy of Sciences of USA (PNAS), Jan. 21, 2003, pp. 438-442, vol. 100, No. 2.
Ando, M. et al., "Formaldehyde Dehydrogenase from *Pseudomonas putida*," J. Biochem., 1979, pp. 1165-1172, vol. 85.
Bennetzen, J.L. et al., "DNA Insertion in the First Intron of Maize Adh1 Affects Message Levels: Cloning of Progenitor and Mutant Adh1 Alleles," Proc. Naatl. Acad. Sci., Jul. 1984, pp. 4125-4128, vol. 81.
Bennetzen, J.L. et al., "The Primary Structure of the *Saccharomyces cerevisiae* Gene for Alcohol Dehydrogenase I," The Journal of Biological Chemistry, Mar. 25, 1982, pp. 3018-3025, vol. 257, No. 6.
Buhot, L. et al., "Hybrid Transcription System for Controlled Plastid Transgene Expression," The Plant Journal, 2006, pp. 700-707, vol. 46.

(Continued)

*Primary Examiner* — Yong Pak
(74) *Attorney, Agent, or Firm* — Kilpatrick Townsend & Stockton LLP

(57) ABSTRACT

Compositions and methods for genetically modifying algae or other photosynthetic eukaryotes to express an alcohol producing enzyme, such as pyruvate decarboxylase (PDC) and alcohol dehydrogenase (ADH) or any other enzymes that also synthesizes methanol, ethanol or butanol are provided. These enzymes are engineered to contain chloroplast targeting sequences which efficiently target xenotypic proteins to the chloroplast. Algae can be stably transformed with the compositions comprising chloroplast targeting constructs containing alcohol producing enzymes whereby the alcohol is produced in the chloroplast of the organism.

15 Claims, 1 Drawing Sheet

(56) References Cited

OTHER PUBLICATIONS

Conway, T. et al., "Promoter and Nucleotide Sequences of the *Zymomonas mobilis* Pyruvate Decarboxylase," Journal of Bacteriology, Mar. 1987, pp. 949-954, vol. 169, No. 3. Conway et al. (1987) J. Bacteriol. 169:949-954.

Daniell, H. et al., "Containment of Herbicide Resistance Through Genetic Engineering of the Chloroplast Genome," Nature Biotechnology, Apr. 1998, pp. 345-348, vol. 16.

Extended European Search Report, European Application No. 08745035.9, Apr. 7, 2010, 7 pages.

European Examination Report, European Application No. 08745035.9, Jul. 21, 2010, 1 page.

Kellermann, E. et al., "Analysis of the Primary Structure and Promoter Function of a Pyruvate Decarboxylase Gene (PDCI) from *Saccharomyces cerevisiae*," Nucl. Acids Res., 1986, pp. 8963-8977, vol. 14.

Lee, C-G. et al.,"High-Density Algal Photobioreactors Using Light-Emitting Diodes," Biotechnology and Bioengineering, 1994, pp. 1161-1167, vol. 44.

Lössl, A. et al., "Inducible Trans-Activation of Plastid Transgenes: Expression of the R. *eutropha phb* Operon in Transplastomic Tobacco," Plant Cell Physiol., 2005, pp. 1462-1471, vol. 46, No. 9.

Magee, A.M. et al., "T7 RNA Polymerase-Directed Expression of an Antibody Fragment Transgene in Plastids Causes a Semi-Lethal Pale-Green Seedling Phenotype," Transgenic Research, 2004, pp. 325-337, vol. I3.

Mason, D.A. et al."A Gain-of-Function Polymorphism in a G-protein Coupling Domain of the Human $\beta_1$-Adrenergic Receptor," The Journal of Biological Chemistry, Apr. 30, 1999, pp. 12670-12674, vol. 274, No. 18.

Mayfield, S.P. et al., "Expression and Assembly of a Fully Active Antibody in Algae," PNAS, Jan. 21, 2003, pp. 438-442, vol. 100, No. 2.

Muhlbauer, S.K. et al., "External Control of Transgene Expression in Tobacco Plastids Using the Bacterial *lac* Repressor," 2005, pp. 941-946, vol. 43.

Neale, A.D. et al., "Pyruvate Decarboxylase of *Zymomonas mobilis*: Isolation, Properties, and Genetic Expression in *Escherichia coli*," Journal of Bacteriology, Mar. 1987, pp. 1024-1028, vol. 169, No. 3.

Sankar, P. et al., "Cloning of Hydrogenase Genes and Fine Structure Analysis of an Operon Essential for H2 Metabolism in *Escherichia coli*," Journal of Bacteriology, Apr. 1985, pp. 353-360, vol. 162, No. 1.

Verma, D. et al., "Chloroplast Vector Systems for Biotechnology Applications," Plant Physiology, Dec. 2007, pp. 1129-1143, vol. 145.

Wilkinson, S.C. et al., "Mercury Accumulation and Volatilization in Immobilized Algal Cell Systems," Biotechnology Letters, 1989, pp. 861-864, vol. 11, No. 2.

Yamaoka, Y. et al., "β-Carotene Production by Dunaliella salina in Fed-Batch and Semi-Continuous Cultures Under Nutrient Supplement," Seibutsu-Kogaku Kaishi, 1994, pp. 111-114, vol. 72.

Australian First Office Action, Australian Application No. 2008237350, Apr. 21, 2011, 3 pages.

PCT International Search Report and Written Opinion, PCT/US08/59294, Jun. 27, 2008, 8 pages.

Siripornadulsil, S. et al., "Molecular Mechanisms of Proline-Mediated Tolerance to Toxic-Heavy Metals in Transgenic Microalgae," The Plant Cell, Nov. 2002, pp. 2837-2847, vol. 14.

Canadian Office Action, Canadian Application No. 2,682,950, Sep. 29, 2011, 2 pages.

European Examination Report, European Application No. 08745035.9, Jun. 13, 2012, 4 pages.

European Examination Report, European Application No. 12178759.2, Oct. 7, 2013, 4 pages.

European Extended Search Report, European Application No. 12178759.2, Dec. 13, 2012, 9 pages.

Indian Office Action, Indian Application No. 6455/CHENP/2009, Mar. 26, 2013, 2 pages.

Rahman, M. et al., "Effects of Manipulation of Pyruvate Decarboxylase and Alcohol Dehydrogenase Levels on the Submergence Tolerance of Rice," Australian Journal of Plant Physiology, CSIRO, Melbourne, AU, Jan. 2001, pp. 1231-1241, vol. 28, No. 12.

\* cited by examiner

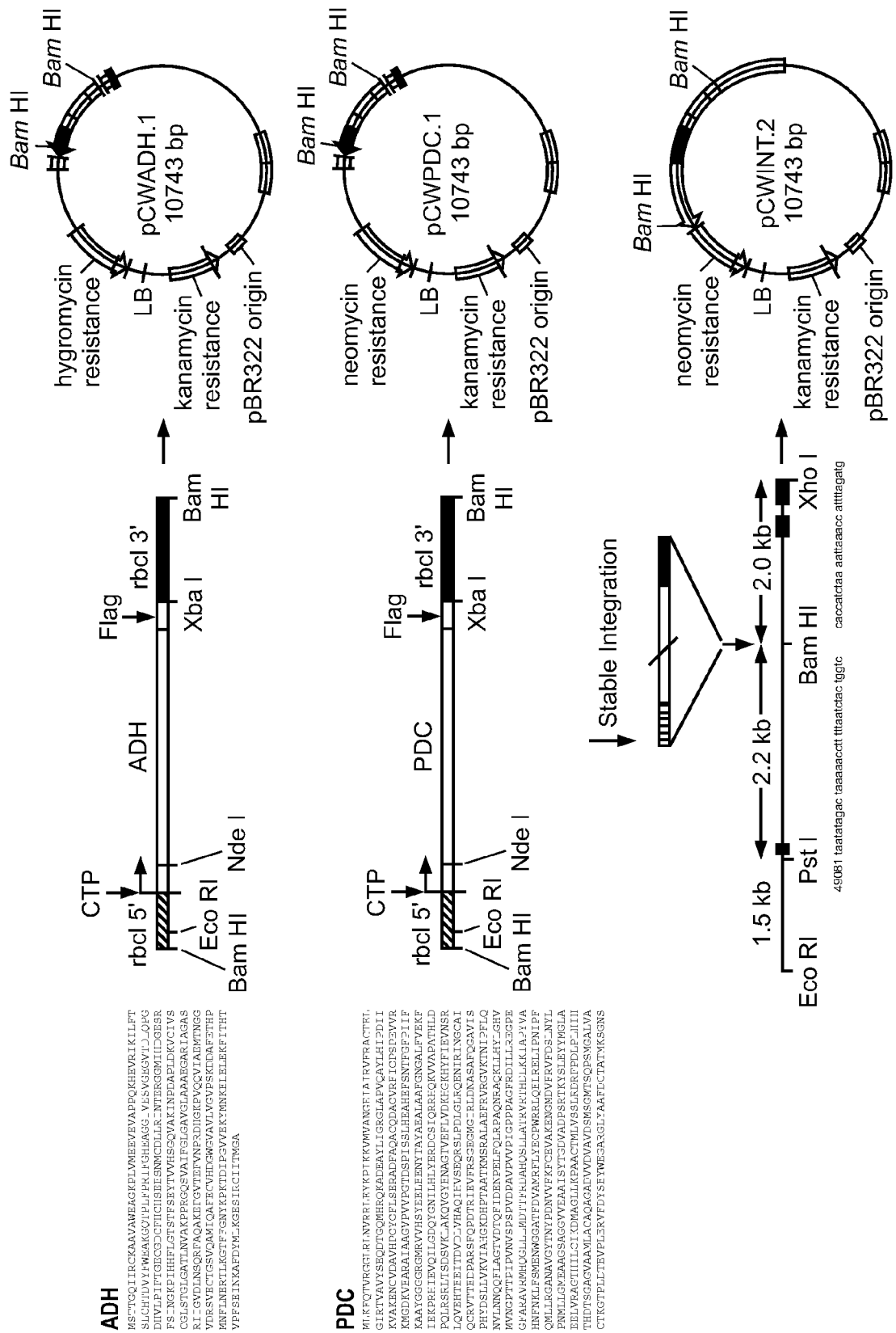

US 9,284,568 B2

METHODS FOR TRANSFORMING EUKARYOTIC ALGAE

CROSS-REFERENCE TO RELATED APPLICATION

This application is the National Stage of and claims priority to International Application No. PCT/US2008/059294, filed Apr. 3, 2008, and claims benefit under 35 U.S.C. §119(e) of U.S. provisional Application No. 60/909,897, filed on Apr. 3, 2007, both of which are incorporated by reference herein in their entirety.

The instant application contains a Sequence Listing which has been submitted via EFS-Web and is hereby incorporated by reference in its entirety. Said ASCII copy, created on Aug. 11, 2015, is named SUBSEQTXT_97724-926724.txt and is 80,739 bytes in size.

FIELD OF INVENTION

The present invention provides compositions comprising elements that specify sequestration in chloroplasts, such as the chloroplast transit peptide (CTP), with ethanol producing enzymes such as pyruvate decarboxylase (PDC) and alcohol dehydrogenase (ADH), or with methanol producing enzymes such as formate dehydrogenase ($F_{ate}$DH), formaldehyde dehydrogenase ($F_{ald}$DH), and alcohol dehydrogenase (ADH), and methods for transforming photosynthetic eukaryotic organisms, particularly algae, using the compositions.

BACKGROUND OF THE INVENTION

Algae are increasingly being used as high density photobioreactors (Lee et al., "High density algal photobioreactors using light emitting diodes" Biotech. Bioengineering 44: 1161-1167 (1994)), in waste water treatments and elimination of heavy metals from contaminated water (Wilkinson "Mercury accumulation and volatilization in immobilized algal cell systems" Biotech. Letters 11: 861-864 (1989)), and for the production of useful products such as β-carotene (Yamaoka Seibutsu-Kogaku Kaishi 72: 111-114 (1994)) and pharmaceutical compounds. Unfortunately, most algae, especially eukaryotic algae, are not amenable to genetic manipulation for specific purposes. Many of the techniques that have been developed for the introduction of DNA into bacterial, yeast, insect, plant and animal cells are not optimal for algal systems, thereby limiting the usefulness of recombinant algae.

Algae, bacteria, and other microorganisms are particularly useful for making fermentation products that include organic acids, such as lactate, acetate, succinate, and butyrate, as well as neutral products, such as ethanol, butanol, acetone, and butanediol. Despite microorganisms producing ethanol, most fuel ethanol is currently still being produced from hexose sugars in corn starch or cane syrup utilizing organisms which metabolize these sugars into ethanol such as *Saccharomyces cerevisiae* or *Zymomonas mobilis*. However, these are relatively expensive sources of biomass sugars, often require fertilizers of fossil fuel origin, and have competing value as foods. Significantly, carbon dioxide is also generated as a by-product of fermentation. This is a property of all fermentative processes which is particularly undesirable as it contributes to atmospheric carbon dioxide.

Various attempts have been made to modify microorganisms to produce ethanol. The genes coding for alcohol dehydrogenase II and pyruvate decarboxylase in various organisms have been cloned and sequenced, and used to transform microorganisms to produce alcohols. For example, recombinant *E. coli* over-expressing *Z. mobilis* pyruvate decarboxylase were shown to have increased production of ethanol, although, very low ethanol concentrations were produced.

A superior approach is to link ethanogenesis to photosynthesis, utilizing sunlight as the main energy source, and carbon dioxide from the atmosphere as the main source of carbon for the synthesis of ethanol. Photosynthetic organisms do not normally express PDC or ADH, however, these genes have been introduced into a number of xenotypic organisms and have been shown to be fully expressed. For example, PDC and ADH genes of *Z. mobilis* have been cloned into a shuttle vector and used to transform the cyanobacterium *Synechococcus*. The PDC and ADH genes were expressed under control of the promoter of the cyanobacterial rbcLS operon which encodes the large and small subunits of ribulose-1,5-bisphosphate carboxylase/oxygenase. As a result of this process, ethanol accumulated in the culture medium, thereby demonstrating the principle that oxygenic photoautotrophic microorganisms can be genetically engineered to produce ethanol. U.S. Pat. No. 6,699,696 describes the genetic engineering of the photosynthetic Cyanobacterium *Synechococcus* sp. strain PCC 7942 to contain construct encoding the PDC and ADH enzymes from the *Zymomonas* mobilis pLOI295 plasmid as a method of producing ethanol. In another example, U.S. Application Publication No. 20030087368 describes the transformation of *Rhodobacter* with ethanogenic enzymes to produce ethanol. However, the use of photosynthetic prokaryotes to produce ethanol fails to generate quantities of ethanol significant or scalable with respect to energy requirements. Notably, this approach does not exploit the inherent efficiencies of enzyme chloroplast targeting.

The present invention relates to the creation and expression of a novel, genetically encoded cassettes coding for the sequestration of efficient ethanol producing systems in the chloroplasts of photosynthetic organisms, particularly eukaryotic algae, thereby producing ethanol in useful quantities.

SUMMARY OF THE INVENTION

The present invention is directed to compositions useful for transforming eukaryotic organisms, particularly eukaryotic algae, for the production of alcohols. The compositions of the invention comprise a DNA sequence encoding for chloroplast transit peptide (CTP), pyruvate decarboxylase (PDC) and/or alcohol dehydrogenase (ADH) for the production of ethanol; or CTP, formate dehydrogenase (FateDH), formaldehyde dehydrogenase (FaldDH), and/or alcohol dehydrogenase (ADH) for the production of methanol, and pyruvate-ferredoxin oxidoreductase, acetyl-CoA-acetyl transferase, hydroxybutyryl-CoA dehydrogenase, Crotonase, butyryl CoA dehydrogenase, phosphobutyrylase, butyrate kinase or combinations thereof for the production of butanol. The enthanogenic enzymes described can be derived from any genetic background, species, or be of synthetic origin.

In one aspect of the invention, the DNA sequence comprises genes encoding for CTP and PDC, CTP and ADH, or CTP, PDC, and ADH, all under the control of heterologous promoters.

In another aspect of the invention, the DNA sequence comprises genes encoding for CTP and $F_{ate}$DH; CTP and $F_{ald}$DH; CTP, $F_{ate}$DH, and ADH; CTP, $F_{ald}$DH, and ADH; CTP, $F_{ate}$DH, and $F_{ald}$DH; or CTP, $F_{ate}$DH, $F_{ald}$DH, and ADH, all under the control of heterologous promoters.

In yet another aspect of the invention, the DNA sequence comprises the genes and CTP described above, as well as flanking sequences that permit permanent integration of DNA encoding the chimeric CTP-enzyme cassettes into either the chloroplast genome, or into the nuclear genome of the target photosynthetic organism, or as a free plasmid.

The present invention also comprises DNA constructs suitable for transforming algal cells to produce or overproduce alcohols. The DNA constructs include a DNA sequence encoding chloroplast transit peptide (CTP), one or more sequences encoding an enzyme capable of producing an alcohol, and a heterologous promoter sequence connected to the 5'-end or 3'-end of the DNA sequence. The promoter will be capable of providing for expression of the enzyme under at least some algal growth conditions. In addition the DNA construct can include flanking sequences that permit stable integration into either the chloroplast genome, or the host nuclear genome. In an exemplary case, the DNA sequence will encode the PDC or ADH gene, or preferably both collinearly, as well as CTP fused to each enzyme. In another exemplary case, the DNA sequence will encode the $F_{ate}DH$, $F_{ald}DH$ and ADH genes, preferably all three, as well as CTP and flanking genome integration sites.

The present invention still further provides for algal cells which are capable of expressing at least one enzyme for producing alcohol, where the enzyme is linked to a CTP. For example, the algal cells are capable of expressing PDC, ADH on separate plasmids, or preferably both on the same plasmids where PDC and/or ADH are attached to CTP. As another example, the algal cells are capable of expressing $F_{ate}DH$, $F_{ald}DH$ and/or ADH on separate plasmids or preferably, all three together each attached to a CTP. Such algal cells can be obtained by transforming algal cells with the DNA constructs described above.

These and other aspects of the present invention will become evident upon reference to the following detailed description.

BRIEF DESCRIPTION OF DRAWINGS

FIG. 1 illustrates the plasmids containing constructs comprised of transit peptides (SEQ ID NOS 8 and 9, respectively, in order of appearance) fused to ethanogenic or methanogenic enzymes. FIG. 1 discloses the nucleotide sequence as SEQ ID NO: 10.

DETAILED DESCRIPTION

I. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); and *Methods In Enzymology* (S. Colowick and N. Kaplan eds., Academic Press, Inc.).

The following amino acid abbreviations are used throughout the text:
Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: H is (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations arising with hosts that produce the proteins or errors due to PCR amplification.

As used herein, the term a "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

A "coding sequence" is an in-frame sequence of codons that correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide in vivo.

As used herein, a "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide.

A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA which is then in turn translated into the protein encoded by the coding sequence. Within the promoter sequence can be found a transcription initiation site (conveniently defined by mapping with nuclease S1), as well as protein binding domains (consensus sequences) responsible for the binding of RNA polymerase.

A "genetic fusion" according to this invention is a chimeric DNA containing a promoter and a coding sequence that are not associated in nature.

A "replicon" is any genetic element (e.g., plasmid, chromosome, virus) that functions as an autonomous unit of DNA replication in vivo; i.e., capable of replication under its own control.

The term "vector" as used herein refers to a replicon, such as plasmid, phage or cosmid, to which another DNA segment may be attached so as to bring about the replication of the attached segment. Vectors can be used to introduce a foreign substance, such as DNA, RNA or protein, into an organism.

A cell has been "transformed" by exogenous DNA when such exogenous DNA has been introduced inside the cell wall. Exogenous DNA may or may not be integrated (covalently linked) to chromosomal DNA making up the genome of the cell.

By "physiological pH" or a "pH in the physiological range" is meant a pH in the range of approximately 7.2 to 8.0 inclusive, more typically in the range of approximately 7.2 to 7.6 inclusive.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

The above-referenced methods for determining homology also may be used to align similar sequences and so identify corresponding positions in two or more sequences (nucleic acid or polypeptide sequences). The two or more sequences may represent splice variants or homologous sequences from different species. While the polymorphisms of the present invention have been described by reference to the coding sequence of particular molecules such as, e.g., the human $\beta_1$-adrenergic receptor as described in GenBank Accession number AF 16900 and in Mason, Moore, Green, and Liggett, "A gain-of-function polymorphism in a G-protein coupling domain of the human beta1-adrenergic receptor," J. Biol. Chem. 274(18), 12670-12674 (1999) (both of which are herein incorporated by reference in their entirety), one of ordinary skill will readily recognize that the invention is intended to encompass polymorphisms occurring in corresponding positions in different sequences.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

The term "wild type" as used herein in reference to a gene, nucleic acid or gene product, especially a protein and/or biological property, denotes a gene, gene product, protein, or biological property predominantly found in nature.

II. Overview

The present invention discloses compositions and methods for producing high levels of alcohol, particularly methanol, ethanol, or butanol, using transgenic algae, particularly eukaryotic algae. The eukaryotic algae can be modified wherein the alcohol producing enzymes are sequestered in the chloroplast of the organism. Thus, in one aspect of the invention, the alcohol producing enzyme is expressed in the cellular nucleus, and then sequestered into the chloroplast for producing high levels of alcohol. In another aspect of the invention, the alcohol producing enzyme is expressed in the cytoplasm of the organism, and then sequestered within the chloroplast for producing high levels of alcohol. In another aspect of the invention, the alcohol producing enzyme is expressed in the chloroplast of the organism, and then sequestered within the chloroplast for producing high levels of alcohol.

In one aspect of the invention, the eukaryotic organisms can be genetically modified to express or overexpress pyruvate decarboxylase (PDC), alcohol dehydrogenase (ADH), or both. The genes encoding PDC and ADH can be of any provenance. The enzymes can be fused to a chloroplast transit peptide (CTP). The CTP directs the PDC and/or ADH to the chloroplast resulting in organisms with ethanogenic enzymes localized in the inner membrane of the chloroplast. The transgenic organisms thus obtained efficiently produce products that would otherwise be obtained by fermentation, such as alcohols, and ethanol in particular.

In another aspect of the invention, the eukaryotic organisms can be genetically modified to express or overexpress formate dehydrogenase ($F_{ate}DH$), formaldehyde dehydrogenase ($F_{ald}DH$), alcohol dehydrogenase (ADH), or all three. The enzymes can be fused to a chloroplast transit peptide (CTP). The CTP directs formate dehydrogenase ($F_{ate}DH$), formaldehyde dehydrogenase ($F_{ald}DH$), and/or alcohol dehydrogenase (ADH) to the chloroplast resulting in organisms with methanolgenic enzymes localized in the inner membrane of the chloroplast. The transgenic organisms thus obtained efficiently produce products that would otherwise be obtained by fermentation, such as alcohols, and methanol in particular.

In another aspect, a vector is provided that codes for chloroplast transit peptide (CTP), pyruvate decarboxylase (PDC) and/or alcohol dehydrogenase (ADH). The vector can be introduced into a eukaryotic organism by viral vector, or physical or chemical means wherein the vector is located in the nucleus of the organism. The transcription of the DNA fragment to the corresponding RNA which is then translated into a chimeric protein comprised of PDC or ADH, and a CTP fused to either the N-terminal or C-terminal end of PDC or ADH, which is subsequently translocated into the chloroplast by the CTP.

In another aspect, a vector is provided that codes for chloroplast transit peptide (CTP), formate dehydrogenase ($F_{ate}DH$), and/or formaldehyde dehydrogenase ($F_{ald}DH$), and/or alcohol dehydrogenase (ADH). The vector can be introduced into a eukaryotic organism by viral vector, or physical or chemical means wherein the vector is located in the nucleus of the organism. The transcription of the DNA fragment to the corresponding RNA which is then translated into a chimeric protein comprised of ($F_{ate}DH$), ($F_{ald}DH$) or ADH, and a CTP fused to either the N-terminal or C-terminal end of ($F_{ate}DH$), or ($F_{ald}DH$) or ADH, which is subsequently translocated into the chloroplast by the CTP.

In another aspect of the invention, a vector is provided. The vector comprises coding sequences for the CTP, PDC, and ADH. In one manifestation a promotor precedes DNA encoding a CTP-PDC chimera. In another manifestation, a promotor precedes DNA encoding PDC-CTP chimera. In another manifestation a promotor precedes DNA encoding a CTP-ADH chimera. In another manifestation a promotor precedes DNA encoding an ADH-CTP chimera. In another manifestation a promotor precedes DNA encoding a CTP-PDC chimera. In another manifestation a promotor precedes DNA encoding a chimera PDC-CTP. In another manifestation a promotor precedes DNA encoding a chimera PDC-CTP separated by untranslated region (UTR) sequences followed by ADH-CTP. In another manifestation a promotor precedes DNA encoding a chimera ADH-CTP separated by untranslated region (UTR) sequences followed by promotor and the chimera PDC-CTP. In another manifestation a promotor precedes DNA encoding a chimera CTP-ADH separated by untranslated region (UTR) sequences followed by promotor and the chimera PDC-CTP. In another manifestation a promotor precedes DNA encoding a chimera ADH-CTP separated by untranslated region (UTR) sequences followed by a promotor and the chimera CTP-PDC. In another manifestation a promotor precedes DNA encoding a chimera CTP-ADH separated by untranslated region (UTR) sequences followed by a promotor and the chimera CTP-PDC. A analogous pattern of constructs can be made for chimeras including ($F_{ate}DH$), or ($F_{ald}DH$) or ADH. The vector can further comprise chloroplast specific UTRs 5' and 3' of each these cassettes whose sequences specify integration sites into the chloroplast genome, or into the photosynthetic organisms nuclear genome for the purposes of stable transformation or other benefits. In addition, enhancer sequences may be included at any locus within the vector described above.

III. Biochemistry of Ethanol Production and Photosynthesis

Algae, bacteria, and other microorganisms are useful for making fermentation products, with the preferred fermentation product being methanol, ethanol, or butanol. In an organism, pyruvate is decarboxylated to form acetaldehyde and acetaldehyde is reduced to form ethanol. These steps are mediated by two enzymes, pyruvate decarboxylase (PDC) and alcohol dehydrogenase (ADH). For present purposes, PDC can be any enzyme which mediates decarboxylation of pyruvate to yield acetaldehyde, and ADH can be any enzyme which mediates reduction of acetaldehyde to ethanol. All the other enzymes required for fermentation are part of the glycolysis system, and they are found in essentially all organisms. Ethanol can also be produced in an acetate/formate/ethanol producing pathway known in both bacteria and algae. The pyruvate-acetaldehyde-ethanol pathway is widely distributed in nature, and is found in bacteria, yeast, algae, and higher plants. A by-product of fermentation is $CO_2$, a green house gas.

By contrast, photosynthetic organisms fix atmospheric carbon, integrate it into energy storing molecules, and release oxygen into the atmosphere. Here too pyruvate is a key compound in the Calvin cycle energy flow during photosynthesis. The initial product of photosynthetic fixation of carbon dioxide is 3-phosphoglycerate, which regenerates ribulose-1,5-biphosphate, the initial acceptor of carbon dioxide. Additional 3-phosphoglycerate is converted into 2-phosphoglycerate, phosphoenolpyruvate and pyruvate. Normally, the energy contained in the pyruvate is directed to the TCA cycle for the synthesis of amino acids, nucleotides, etc. This invention contemplates redirecting this pyruvate into pathways that convert it into ethanol. This reaction produces acetaldehyde which is then converted to ethanol by alcohol dehydrogenase (ADH).

To convert the carbohydrate reserves into ethanol, carbohydrates must be diverted to the glycolytic and phosphogluconate pathways. Although ethanol synthesis will naturally compete with cell growth and reproduction, in this application there is no need for the genetically modified algae to reproduce rapidly and grow beyond the amounts necessary to produce and maintain an adequate population for purposes of ethanol production. Thus, it is acceptable for cell division to halt so that algae that utilize only the amount of pyruvate sufficient for cell maintenance, and divert all other metabolic carbon fixation to ethanol production. However, because the presence of alcoholgenic enzymes is selected for and enforced by imposed genetic or biochemical requirements (such as auxotrophic need, and/or antibiotic and/or chemical selection) the invention selects for, or genetically generates, a subset of algae that are successful supporting 1) the production of alcohol, 2) metabolic processes that maintain viability and 3) Algal replication. This selection can occur both naturally, and can be deliberately genetically induced. Optionally, as a means of preserving algal viability, chemical switches can be included such that carbon flow within each cell in the population can be controlled systematically. For example the promoters that govern the transcription of alcoholgenic proteins can be regulated by exogenous inducers, or regulators that govern the translation, or even the degradation of these alcoholgenic can be included specifically in the alcholgenic constructs, or in the total algal genome, so that the production of alcohol producing proteins is not continuous, but occurs only in response to an external inducer. This would permit algae to replicate and metabolize normally, in a manner that permits maintenance of algal stocks without the burden of producing alcohol or alcoholgenic protein, but would then allow the process of alcohol production to be initiated at will, by the introduction of inducers. As exampled, the chloroplast transgene could be place under the transcriptional regulation of an inducible factor that is co-introduced to the nuclear genome (e.g. T7 polymerase L. Buhot et al *Plant J* 46 (2006), pp. 700-707. Lossl et al *Plant Cell Physiol* 46 (2005), pp. 1462-1471 Magee et al, *Transgenic Res V* 13 (2004), pp. 325-33 or to the chloroplast genome (e.g. the lac repressor [Muhlbauer et al *Plant J* 43 (2005), pp. 941-946.].

In the case of methanol production, carbon dioxide reduction is directly converted into methanol via a series of enzymatically coupled sequential reductions catalyzed by three different dehydrogenases. Overall, the process involves an initial reduction of $CO_2$ to formate catalyzed by formate dehydrogenase ($F_{ate}DH$), followed by reduction of formate to formaldehyde by formaldehyde dehydrogenase ($F_{ald}DH$), and finally formaldehyde is reduced to methanol by alcohol dehydrogenase (ADH). In this process, reduced nicotinamide adenine dinucleotide (NADH) acts as a terminal electron donor for each dehydrogenase-catalyzed reduction. These enzymes are traditionally considered methanol detoxifiers, converting methanol into $CO_2$. However this enzymatic pathway exploits the fact that catalyzed reactions can run in both directions, and in presence of plentiful $CO_2$ the back reaction to produce methanol is favored.

Similarly, butanol production can be engineered by expression of pyruvate-ferredoxin oxidoreductase, acetyl-CoA-acetyl transferase, hydroxybutyryl-CoA dehydrogenase, Crotonase, butyryl CoA dehydrogenase, phosphobutyrylase, butyrate kinase or combinations thereof. The sequences of the enzymes are known as shown by the representative sequences provided below:

```
Acetyl-CoA acetyltransferase [Clostridium acetobutylicum]
                                                               (SEQ ID NO: 1)
    1 mkevviasav rtaigsygks lkdvpavdlg ataikeavkk agikpedvne vilgnvlqag
   61 lgqnparqas fkaglpveip amtinkvcgs glrtvslaaq iikagdadvi iaggmenmsr
  121 apylannarw gyrmgnakfv demitdglwd afndyhmgit aeniaerwni sreeqdefal
  181 asqkkaeeai ksgqfkdeiv pvvikgrkge tvvdtdehpr fgstieglak lkpafkkdgt
  241 vtagnasgln dcaavlvims aekakelgvk plakivsygs agvdpaimgy gpfyatkaai
  301 ekagwtvdel dliesneafa agslavakdl kfdmnkvnvn ggaialghpi gasgarilvt
  361 lvhamqkrda kkglaticig ggqgtaille kc 3-hydroxybutyryl-CoA dehydrogenase [Clostridium acetobutylicum]
                                                               (SEQ ID NO: 2)
    1 mkkvcvigag tmgsgiaqaf aakgfevvlr dikdefvdrg ldfinknlsk lvkkgkieea
   61 tkveiltris gtvdlnmaad cdlvieaave rmdikkqifa dldnickpet ilasntssls
  121 itevasatkr pdkvigmhff npapvmklve virgiatsqe tfdavketsi aigkdpveva
  181 eapgfvvnri lipmineavg ilaegiasve didkamklga nhpmgplelg dfigldicla
  241 imdvlysetg dskyrphtll kkyvragwlg rksgkgfydy sk Crotonase [Clostridium perfringens]
                                                               (SEQ ID NO: 3)
    1 meniifnesn giaeviinrp kalnalnnqt itelgevine iskrkdiktv iitgagekaf
   61 vagadivemk dlnsmeardf srlaqkvfsd ienmpqivia avngyalggg celsmacdir
  121 laskkakfgq pevnlgilpg fagtqrlprl vgkgiakeli fstdmidaee ahriglankv
  181 yepeelmdka relankimsk spvgvrlaka ainnglnmdt esaynyeadl falcfstedq
  241 legmnafvdk rkadfkdk Butyryl-CoA dehydrogenase [Clostridium acetobutylicum]
                                                               (SEQ ID NO: 4)
    1 mdfnltreqe lvrqmvrefa enevkpiaae ideterfpme nvkkmgqygm mgipfskeyg
   61 gaggdvlsyi iaveelskvc gttgvilsah tslcasline hgteeqkqky lvplakgeki
  121 gayglteрna gtdsgaqqtv avlegdhyvi ngskifitng gvadtfvifa mtdrtkgtkg
  181 isafiiekgf kgfsigkveq klgirasstt elvfedmivp venmigkegk gfpiamktld
  241 ggrigiaaqa lgiaegafne araymkerkq fgrsldkfqg lawmmadmdv aiesarylvy
  301 kaaylkqagl pytvdaarak lhaanvamdv ttkavqlfgg ygytkdypve rmmrdakite
  361 iyegtsevqk lvisgkifr Butyrate kinase [Clostridium acetobutylicum]
                                                               (SEQ ID NO: 5)
    1 myrlliinpg ststkigiyd dekeifektl rhsaeeieky ntifdqfqfr knvildalke
   61 anievsslna vvgrggllkp ivsgtyavnq kmledlkvgv qgqhasnlgg iianeiakei
  121 nvpayivdpv vvdeldevsr isgmadiprk sifhalnqka varryakevg kkyedlnliv
  181 vhmgggtsvg thkdgrviev nntldgegpf spersggvpi gdlvrlcfsn kytyeevmkk
  241 ingkggvvsy lntidfkavv dkalegdkkc aliyeaftfq vakeigkcst vlkgnvdaii
  301 ltggiayneh vcnaiedrvk fiapvvrygg edellalaeg glrvlrgeek akeyk
```

In the practice of the invention, the DNA constructs disclosed herein can be introduced into eukaryotic algae alone or as part of a DNA vector. Any type of vector can be used, as those skilled in the art are well able to construct vectors and design protocols for recombinant gene expression, for example in eukaryotic algae. Suitable vectors can be chosen or constructed, containing chloroplast targeting sequence, PDC coding region, ADH coding region, ($F_{ate}DH$) coding region, ($F_{ald}DH$) coding region, or coding regions for pyruvate-ferredoxin oxidoreductase, acetyl-CoA-acetyl transferase, hydroxybutyryl-CoA dehydrogenase, Crotonase, butyryl CoA dehydrogenase, phosphobutyrylase, butyrate kinase or combinations thereof, as appropriate, regulatory sequences, including promoter sequences, terminator fragments, polyadenylation sequences, enhancer sequences, marker genes and other sequences as appropriate.

VI. Chloroplast Targeting Sequences and Proteins

Chloroplasts, like mitochondria, are organelle surrounded by a multi-celled composite membrane and have their own DNA. In one aspect of the invention, the chloroplast DNA can be engineered to produce alcohols. In another aspect of the invention, a gene fusion construct can be made where a chloroplast transit sequence peptide is fused to alcohol producing enzymes and the transit peptide facilitates the translocation of the alcohol producing enzymes into the chloroplasts.

Thus, in one aspect of the invention, a gene fusion construct is transformed into chloroplasts of the host cells. Numerous methods are available in the art to accomplish chloroplast transformation and expression (Daniell et al. (1998) Nature Biotechnology 16:346). In general, the expression construct comprises a transcriptional regulatory sequence functional in plants operably linked to a gene fusion construct. Expression cassettes that are designed to function in chloroplasts include the sequences necessary to ensure expression in chloroplasts. Typically, the coding sequence is flanked by two regions of homology to the chloroplastid genome to effect a homologous recombination with the chloroplast genome; often a selectable marker gene is also present within the flanking plastid DNA sequences to facilitate selection of genetically stable transformed chloroplasts in the resultant transplastonic plant cells.

Thus, the pdc and/or adh genes can be fused to a chloroplast targeting sequence in order to integrate the pdc and/or adh genes into the chloroplast DNA, and the replication of the chloroplast DNA produces the PDC and/or ADH enzymes in the chloroplast. In addition the ($f_{ate}$dh), and/or ($f_{ald}$dh) and/or adh genes can be fused to a chloroplast targeting sequence in order to integrate the ($f_{ate}$dh) and/or ($f_{ald}$dh) and/or adh genes into the chloroplast DNA, and the replication of the chloroplast DNA produces the PDC and/or ADH enzymes or ($F_{ate}$DH), or ($F_{ald}$DH) or ADH in the chloroplast. Examples of such chloroplast targeting sequences include the small subunit of ribulose-1,5-biphosphate carboxylase (ss-RUBISCO, SSU), 5-enolpyruvateshikimate-3-phosphate synthase (EPSPS), ferredoxin, ferredoxin oxidoreductase, the light-harvesting-complex protein I and protein II, and thioredoxin F. Those skilled in the art will also recognize that various other chimeric constructs can be made that utilize the functionality of a particular targeting sequences to import the PDC and/or ADH enzymes and other alcoholic enzymes into the chloroplast.

In another aspect, chloroplast targeting proteins (CTPs) facilitate the translocation of the alcohol producing enzymes into the chloroplast. The CTPs do not have a consensus sequences, but, despite the lack of consensus sequence, do share characteristic properties. CTPs are comprised of about 40 to 100 amino acids, are virtually devoid of negatively charged amino acids, their N-termini lack charged amino acids, and their central region contains a very high proportion of basic or hydroxylated amino acids, such as serine or threonine while the C-termini are arginine rich. Further, CTPs generally form amphipathic, beta-sheet secondary structure. Targeting peptides that favor the intraluminal space are usually bipartite, and, in all cases, the CTPs are cleaved after importation.

Thus, a chloroplast targeting peptide suitable for use in accordance with the present invention can be any peptide sequence which directs a polypeptide to the chloroplast of a plant cell. Suitable peptides may readily be identified by a skilled person and some examples are shown in Table 1 (SEQ ID NOS:11-27, respectively, in order of appearance).

TABLE 1

Exemplary chloroplast targeting peptides

| Accession No | gene | Species |
| --- | --- | --- |
| P32260 gi\|12644209 | cysteine synthase chloroplast precursor | Spinacia oleracea |
| AAG59996 gi\|12658639 | ferredoxin: sulfite reductase precursor | Glycine max |
| S10200 gi\|100078 | carbonate dehydratase precursor | Pisum sativum |
| CAB89287 gi\|7672161 | chloroplast ftsZ-like protein | Nicotiana tabacum |
| P17067 gi\|115471 | carbonic anhydrase, chloroplast precursor (carbonate dehydratase) | Pisum sativum |
| AAD22109 gi\|4530595 | heme oxygenase 2 | Arabidopsis thaliana |
| AAD22108 gi\|4530593 | heme oxygenase 1 | Arabidopsis thaliana |
| AAC50035 gi\|450235 | aps kinase | Arabidopsis thaliana |
| AAC12846 gi\|1051180 | phytoene desaturase | Zea mays |
| AAB87573 gi\|2645999 | chlorophyll a/b binding protein of LHCIIi type I precursor | Panax ginseng |
| FEKM gi\|7427604 | ferredoxin [2Fe-2S] precursor | Chlamydomonas reinhardtii |
| CCKM6R gi\|2144284 | cytochrome c6 precursor | Chlamydomonas reinhardtii |
| P23577 gi\|118044 | APOCYTOCHROME F PRECURSOR | Chlamydomonas reinhardtii |
| P93407 gi\|3915008 | superoxide dismutase [CU-ZN], chloroplast precursor | Oryza sativa |
| Q96255 gi\|3914996 | phosphoserine aminotransferase, chloroplast precursor | Arabidopsis thaliana |
| O24600 gi\|3914826 | DNA-directed RNA polymerase, chloroplast precursor | Arabidopsis thaliana |
| O49937 gi\|3914665 | 50S ribosomal protein L4, chloroplast precursor | Spinacia oleracea |

Other examples can be found in various databases, for example, the NCBI database or the CHLPEP—A database of chloroplast transit peptides.

V. Alcohol Coding Regions

The present invention comprises nucleic acid molecules encoding for an alcohol producing enzyme. The enzyme can be for any alcohol, preferably an aliphatic alcohol, such as, for example, methanol, ethanol, propanol, isopropanol, butanol, pentanol, hexanol, and the like. For example, when the alcohol is selected to be ethanol, the nucleic acid molecules encoding for the enzyme comprise pyruvate decarboxylase genes (pdc) that encode the enzyme pyruvate decarboxylase (PDC), alcohol dehydrogenase genes (adh) that encode the enzyme alcohol dehydrogenase (ADH), or combinations thereof. The pdc and adh genes can be derived from any organism. PDC has been cloned from, and can be obtained from, both yeast (Kellerman et al. (1986) Nucl. Acids Res. 14:8963-8977) and bacteria (Neale et al. (1987) J. Bacteriol. 169:1024-1028). ADH has been cloned from, and can be obtained from, several sources, including bacteria (Conway et al. (1987) J. Bacteriol. 169:949-954), higher plants (Bennetzen et al. (1984) PNAS USA 81:4125-4128) and yeast (Bennetzen et al. (1982) J. Biol. Chem. 257:3018-3025). For use in the present invention, PDC and/or ADH can be obtained from any plant, yeast or bacterial source. Animal sources of ADH can also be used but are less desirable, since allosteric characteristics may be suited to the metabolism rather than the production of alcohol. Formaldehyde dehydrogenase was originally cloned from *Pseudomonas putida* (Ando, M., T. et al. J. Biochem. 85:1165-1172.) Formate dehydrogenase was originally cloned from *E. Coli* (Sankar P. et al J. Bacteriol. 1985 April; 162(1):353-60). The $F_{ate}DH$ and $F_{ald}DH$ genes can be derived from any organism, and use in the present invention, $F_{ate}DH$ and/or $F_{ald}DH$ can be obtained from any plant, yeast or bacterial source.

The coding sequence for yeast PDC is given in Kellerman et al. (1986), and the coding sequence for yeast ADH is given in Bennetzen (1982). However, the pdc nucleic genes and adh genes can be derived from any organism, including bacterial sources such as *Acidobacter, Aeromonas, Alcaligenes, Bacillus, Bacteroides, Bradyrhizobium, Enterococcus, Escherichia, Gluconobacter, Halochromatium, Lactobacillu, Lactococcus, Rhizobium, Rhodobacter, Rhodococcus, Rhodospirillum, Shewanella, Sphingobacterium, Sphingomonas, Streptococcus, Succinomonas, Thermobifida, Zymobacter* (e.g., Zymobacter palmae), *Zymomonas* (e.g., *Zymomonas* mobilis), and the like.

The pdc and adh genes can be cloned from a yeast library by known methods. Coding sequences for PDC and ADH can be obtained by standard techniques, for example, PCR amplification of cDNA. In another method, a cDNA library can be screen with probes developed using the known sequences of PDC and ADH.

In another aspect of the invention, an isolated gene includes coding sequences for PDC and ADH and adjacent 5' and/or 3' regulatory sequences from the chromosomal DNA of the organism from which the genes are derived (e.g., adjacent 5' and/or 3' pdc regulatory sequences). Preferably, an isolated gene contains less than about 10 kb, 5 kb, 2 kb, 1 kb, 0.5 kb, 0.2 kb, 0.1 kb, 50 bp, 25 by or 10 by of nucleotide sequences which naturally flank the gene in the chromosomal DNA of the organism from which the gene is derived.

In another aspect of the invention, mutant or chimeric pdc and/or adh genes can be used. Typically, a mutant gene includes a gene having a nucleotide sequence which includes at least one alteration (e.g., substitution, insertion, deletion) such that the polypeptide or polypeptide that can be encoded by the mutant exhibits an activity that differs from the polypeptide or polypeptide encoded by the wild-type nucleic acid molecule or gene. Typically, a chimeric pdc includes an entire domain derived from another PDC that is engineered (fused, exchanged) with a corresponding domain in a PDC. Preferably, a mutant nucleic acid molecule or mutant gene encodes for a PDC or ADH polypeptide having improved activity, such as, for example, improved substrate affinity, improved thermostability, activity at a different pH, improved expression in the host cell, resistance to product feedback inhibition, resistance to proteolytic degradation and the like.

IV. Promoter Sequences

Promoter sequences can be obtained from bacterial, yeast, algae, or any other source. Preferably, the promoter sequences are isolated from the potential host organism or a closely related organism. Promoters that are functional in higher plants are preferred for groups of algae closely related to higher plants. For example, the promoter can be the atpA promoter, the 35S CaMV promoter, CaMV 35S promoter, ribulose bisphosphate carboxylase small subunit gene (SSU), the nopaline synthase promoter, polyadenylation sequences from the Ti plasmid of *Agrobacterium tumefaciens*, the rbcL promoter, the promoter region of the tubB2 gene from *Chlamydomonas reinhardtii*, the PL promoter from bacteriophage, the bacterial tip promoter, and the like.

In another aspect of the invention, the promoter can be a gene associated with photosynthesis in a photosynthetic species and that can be used to direct expression of a protein in transformed algal cells. Preferred promoters are those for genes from other photosynthetic species, including other algae and cyanobacteria, which are homologous to the photosynthetic genes of the algal host to be transformed. For example, a series of light harvesting promoters from the fucoxanthin chlorophyll binding proteins have been identified and cloned from Phaeodactylum tricornutum and the fcp promoters can be used for transformation of algae. Suitable promoters include the fcpA, fcpB, fcpC, and fcpE promoters, as well as any lhc promoter.

DNA constructs according to the invention can be made using standard techniques. In a preferred embodiment, the promoter is positioned on the 5' or upstream side of a coding sequence whose expression is desired. Optionally, reporter gene or selectable markers can be linked to the promoter. In addition, host or zenotypic enhancer regions in the 5' region or 3' regions can be linked to the promoter. In addition an inducible element may be included on the promoter, triggered either by light or it absence, or chemically induced. An example of an inducible promoter is the tobacco PR-1a gene which is inducible by chemical activators of the systemic acquired resistance pathway such as BTH, which can be plugged into algae (Biont, Actigardt). The linked construct can be inserted into the alga and the expression of the reporter can be measured.

Downstream or 3' of the light harvesting protein promoter are fused one or more additional protein coding sequences, such as genes for CTP, PDC, and/or ADH. Alternatively, both protein coding sequences can be introduced, each under the control of a different promoter and having one, two, or more selectable markers located on a single molecule.

In addition, the construction used preferably has a selectable marker, a screenable marker or both. Examples of selectable markers include NPTII conferring kanamycin resistance, HPT conferring hygromycin resistance, DHFR Mtx conferring methotrexate resistance, and SPT conferring streptomycin resistance. Thus, selectable markers include resistances to kanamycin, hygromycin, spectinomycin, streptomycin, sulfonyl urea and other drugs for which corresponding resistance genes can be used in the practice of the invention.

One particularly useful selectable marker which can be used is the Sh ble gene which encodes the bleomycin binding protein from *Streptoalloteichus hindustanus*, and has been used as a selectable marker for genetic transformations of many organisms, including bacteria, microalgae, fungi, protozoa, plants, and animal cells. The bleomycin binding protein, encoded by the ble gene, confers resistance to several antibiotics, including bleomycin, phleomycin, and Zeocin™. Zeocin™ and phleomycin have been found to be particularly potent in inhibition of the growth of eukaryotic algae. Zeocin™ or phleomycin or other related antibiotics can be used interchangeably for selection with this marker. Thus, the sh ble gene has been found to function as a resistance determinant in algae, and use of the sh ble gene on transforming DNA in combination with a zeocin or phleomycin-type selection affords a convenient selection for transformants of eukaryotic algae.

Other useful protein coding sequences which may be fused to the upstream promoter include resistance determinants for herbicides, heavy metals, high pH or salt. Examples of non-selectable transformation markers are GUS, LUC, GFP and YFP (one for ADH and one for PDC). Expression of GFP/YFP allow the determination of percent of algae that are transformed, the percentage of algae translating the desired proteins, as well as the level of expression for each individual cell via FACS analysis whereas GUS and LUC give only the average expression for a given population of algae analyzed. As will be evident to one of skill in the art, ADH and/or PDC can also be used as a screenable marker, in addition to their engineering function. Marker genes are included to facilitate the isolation of transformants. They are desirable if the frequency of transformation is low enough that it is not convenient to screen plants for the gene of interest by, for example southern blot analysis, or PCR analysis. Selectable markers are desirable especially if the frequency of transformation is low enough that it is not convenient to screen for transformants.

VII. 3' Nontranslated Regulatory Region

Optionally, when necessary for efficient gene expression, the expression cassette can include a 3' nontranslated regulatory DNA sequence. The 3' nontranslated regulatory DNA sequence preferably includes from about 3 to 1000 nucleotide base pairs (bp) and contains transcription and/or translation termination sequences. The 3' nontranslated regions can be obtained from the flanking regions of genes from algae, yeast, bacterial, plant, or other eukaryotic cells. For transcription efficiency and termination of a first DNA sequence encoding one or more alcohol gene, the 3' flanking sequences can vide for gene expression in algae, particularly eukaryotic algae, by standard methodologies.

Specific examples of the 3' nontranslated regulatory DNA sequences functional in eukaryotic cells include about 500 by of 3' flanking DNA sequence of the pea ribulose biphosphate carboxylase small subunit E9 gene, 3' flanking DNA sequence of the octopine synthase gene, the 3' flanking DNA sequence of the nopaline synthase gene, and SV40 polyadenylation and transcription termination sequences. Especially preferred are the 3' nontranslated regulatory DNA sequences that function in plant cells such as the 3' flanking DNA sequence from the octopine synthase or nopaline synthase genes.

The 3' nontranslated DNA regulatory regions are often already present in plasmid vectors used for selection amplification and transformation of algae. Typically, the gene sequence encoding for ADH, PDC, or both and CTP are inserted immediately upstream from 3' nontranslated DNA regulatory sequence so that the DNA sequences are operably linked together. Alternatively, the 3' nontranslated DNA regulatory regions known to be functional in a particular algae can be isolated from a cloned gene sequence by restriction endonuclease digestion. Once isolated, the 3' flanking region DNA sequence can be inserted downstream from the first or second DNA sequence by standard subcloning methods.

VIII. Vectors

Suitable vector systems for carrying the gene constructs into the host cells include, for example, plasmids, viruses, phages, and yeast artificial chromosomes (YAC's). Vectors include additional DNA sequences that provide for easy selection, amplification, and transformation of the expression cassette in algae, particularly eukaryotic algae. The additional DNA sequences include origins of replication to provide for autonomous replication of the vector, selectable marker genes preferably encoding antibiotic resistance, unique multiple cloning sites providing for multiple sites to insert the expression cassette, and sequences that enhance transformation of the algae cells. A number of different backbone vectors used in plant eukaryotes are suitable, sharing a number of features that would be common to vectors used in this application. A table from a recent review Verma et al Plant Physiology 145:1129-1143 (2007) summarizes some of the features likely to be shared amongst these vectors. For

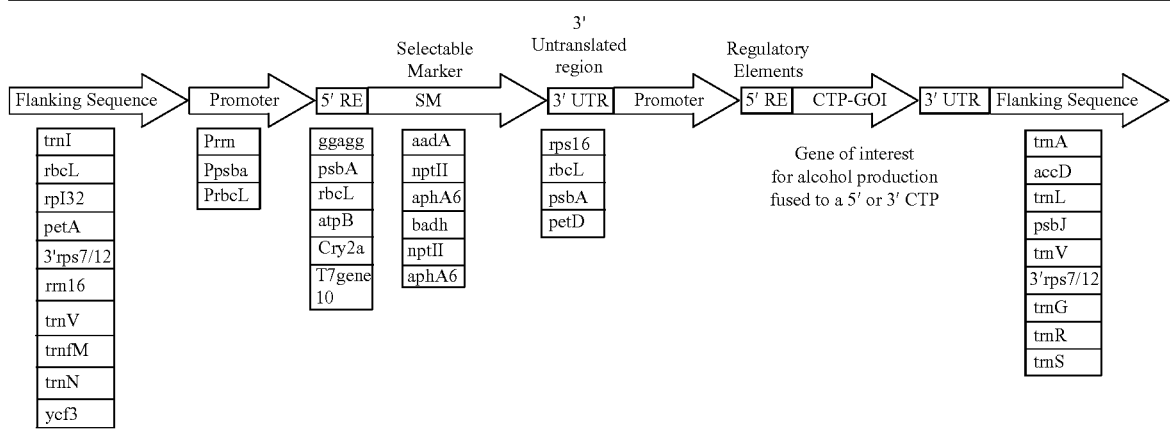

include a transcription termination sequence, as well as a polyadenylation sequence that functions to add a polyA tail to the messenger RNA. The 3' nontranslated regions are operably linked to the first and/or second DNA sequence to pro- C. reinhardtii chloroplasts vectors under the control of the ATPase alpha subunit (atpA) or psbA promoter and 5' untranslated regions (UTRs) and the rubisco large subunit (rbcL) 3' UTR have been used with success. Preferred vectors of the invention are plasmid vectors, such as the ColEI plasmid vector, such as pUC18 and pUC19, the binary $T_i$ vector pGA582, the pCW vector, or tobacco chloroplast transformation vector pLD-CtV previously developed in the Daniell laboratory (Daniell et al., 1998, 2001a; Guda et al., 2000; DeCosa et al., 2001). Although flanking sequense for homologous recombination into the chloroplasts are common in these vectors, they are included but not essential for this application, which utilizes CTPs to target translated protein to the chloroplast, regardless of the source of translation. Any vector usable in algae can be used as vectors into which the above operon capable of being expressed can be introduced. Examples of such vectors include pUC104 and pUC105, pLS103, pDPL13, pUC303, pSG111, pPUC29, pPLAN Bal, pBAS18, and the like.

In general, the upstream DNA sequences of a gene expressed under control of a suitable promoter can be restriction mapped and areas important for the expression of the protein characterized. The exact location of the start codon of the gene can be determined and a vector can be designed for expression of a heterologous protein by removing the region responsible for encoding the gene's protein but leaving the upstream region found to contain the genetic material responsible for control of the gene's expression. A synthetic oligonucleotide is preferably inserted in the location where the protein sequence once was, such that any additional gene could be cloned in using restriction endonuclease sites in the synthetic oligonucleotide. A coding sequence inserted at this site would then be under the control of an extant start codon and upstream regulatory region that will drive expression of the foreign protein encoded by this gene. The gene for the desired protein present in a cloning vector can be introduced into the host organism using any of several methods. Manipulation of conditions to optimize transformation for a particular host is within the skill of the art.

An exemplary vector for use in the practice of the invention is provided in FIG. 1. Two CTP sequences were used, one derived from chlamydomonas reinhardtii rubisco (MKSSAVSAGQRVGGARVATRSVRRAQL) (SEQ ID NO: 6) and the other from chlamydomonas ferredoxin (MRSTFAARVGAKPAVRGARPASR) (SEQ ID NO: 7). These CTP sequences can be used in oligonucleotides to make the BamH1 restriction site on the N-termini of ADH and/or PDC by PCR, or on the C-termini. The adh and pdc gene sequences were cloned from a yeast library. The vector for transformation with ADH (pCWADH.1) contains a hygroymycin selectable marker. The vector for transformation with PDC (pCW-PDC.1) contains a neomycin selectable marker. The vector for transformation with ADH and PDC ((pCWINT.2) contains both selectable markers.

IX. Transformation Systems

Transformed cells can be produced by introducing the vectors described above into a population of target cells and selecting the cells which have taken up the vector, usually by measuring expression of some determinant present on the exogenous DNA but missing from the untransformed cells. These include selective markers, or markers that permit visualization of transformed cells. For example transformed cells are selected via antibiotics encoded within the vectors, with multiple vectors selected simultaneously with multiple antibiotics. In addition, transformed cells are selected by fluorescent markers expressed by the introduced vector, and positive cells are sorted via Fluorescence Activated Cell Sorting (FACS). Ultimately, stable cells lines are selected, obviating the need for continuous antibiotic selection. The basic techniques used for transformation and expression in algal systems are known in the art and can be used in the present invention.

Constructs used in transformation include a construct with CTP and at least one of PDC and ADH, driven by an appropriate promoter, and with an appropriate 3' untranslated region. The construct may contain coding and associated non-coding sequences for both PDC and ADH, and may contain in addition, coding and associated non-coding regions for one or more selectable or screenable markers. The 5' and 3' non-coding regions may be the same for all genes, or they may be different. If the construct contains only one of PDC or ADH, then it may be necessary to make an additional similar construct but for the gene not already incorporated.

DNA constructs formed from gene fusions are delivered to algae using any of the delivery techniques, including either DNA viruses or RNA viruses as transport vehicles, electroporation, PEG induced uptake, and ballistic delivery of DNA. The basic techniques used for transformation and expression in algal systems are known in the art and can be used in the present invention. Any method for introduction of the fusion construct into algae can be used. The known methods include the use of electroporation, DNA-coated particle bombardment, vigorous agitation in the presence of glass beads which renders some of the algal cells permeable to nucleic acids, and the like. Any of the algae species can be used, including Enteromorpha linza, Enteromorpha intestinalis, Ulva pertusa, Ulva taeniata, Monostroma zostericola in the Chlorophyta, as well as members of Genera Laminaria, Undaria, Macrocystis, Sargassum and Dictyosiphon in the Phaeophyta and Porphyra, Chondrus, Gelidium and Agardhiella in the Rhodophyta.

Ethanol production in algae can be engineered by expressing PDC and ADH in the host cells, using DNA constructs and transformation methods as described below. PDC and ADH activities are preferably high enough that competitive pathways account for less than 50% of carbon flow, and most preferably less than 10%. Methanol production can be engineered by expression of formate dehydrogenase ($F_{ate}DH$), formaldehyde dehydrogenase ($F_{ald}DH$), and alcohol dehydrogenase (ADH), while butanol production can be engineered by the expression of pyruvate-ferredoxin oxidoreductase, acetyl-CoA-acetyl transferase, hydroxybutyryl-CoA dehydrogenase, Crotonase, butyryl CoA dehydrogenase, phosphobutyrylase, or butyrate kinase and combinations thereof.

Transformants engineered with PDC alone can be screened for PDC activity. This screening can be done in both aerobic and anaerobic conditions. PDC can be assayed using well known methods (Neale et al. (1987) J. Bacteriol. 169:1024-1028), for example, in a reaction mix which includes pyruvate, NADH and ADH, pyruvate decarboxylase activity results in production of acetaldehyde, which, in a reaction catalyzed by ADH, produces alcohol and results in oxidation of NADH, which can be measured spectrophotometrically. Alternatively, reactions can be coupled to the production of colored form of pigments, to screen for enzyme activity in culture plates. For example, culture media that includes pararosaniline reacted with sodium bisulfite to produce the leuco form of the dye (Schiff reagent), will react with aldehydes to form an intense red pigment, which can be a screen for aldehyde production. Direct analysis via gas chromatography, specific gravity or other rapid methods can also be employed in alcohol detection and quantification. Presence of PDC expression can be verified by western blot. Numerous anti-PDC antibodies are commercially available such as Pyruvate Dehydrogenase E2 antibody—Azide free (ab37853) from the company abcam for example. Localization of the enzyme in the chloroplast is verified using commercially available chloroplast purification kits, such as CPISO Sigma Chloroplast Isolation Kit, in combination with western blotting.

Transformants engineered with ADH alone can be screened for ADH activity. ADH can be measured using a reaction mix which includes alcohol and NAD+. This reaction produces acetaldehyde and results in reduction of NAD+ to NADH, which can be measured spectrophotometrically. Alternatively, reactions can be coupled to the production of colored form of pigments, to screen for enzyme activity in culture plates. This can be done, for example, by including Schiff reagent and alcohol in culture media where ADH activity results in conversion of alcohol to acetaldehyde, which reacts with Schiff reagent to produce an intensely red color. Presence of expressed enzyme is verified by western blot. Numerous anti-ADH antibodies are commercially available such as Alcohol Dehydrogenase antibody (ab24434) from the company abcam for example. Localization of the enzyme in the chloroplast is verified using commercially available chloroplast purification kits, such as CPISO Sigma Chloroplast Isolation Kit, in combination with western blotting.

Cell lines thus selected for the production of PDC can be used as hosts for transformation with ADH, or they are combined with cell lines high in ADH by sexual crossing or by protoplast fusion, to produce lines that have both ADH and PDC activities. Alternatively, cell lines that are high in ADH can be used as hosts for transformation with PDC, or they are combined as described above. Alternatively, a vector containing both PDC and ADH can be used to transform algae to produce alcohol.

Transformants engineered with both PDC and ADH, can be screened for alcohol production under both aerobic and anaerobic conditions. Alcohol can be detected by well known methods, e.g., in a reaction mix including NAD+ and ADH, in which alcohol is converted to acetaldehyde, resulting in reduction of NAD+, which can be detected spectrophotometrically. Alternatively, reactions can be coupled to the production of colored form of pigments, to screen for enzyme activity in vivo. For example, filter paper soaked with a reaction mix that includes ADH, NAD+ and Schiff reagent, will convert alcohol to acetaldehyde, after which the Schiff reagent reacts with the aldehyde to form an intense red pigment.

The use of the compositions and methods of the present invention for intra-chloroplast targeting can provide enzymes levels of ADH and PDC to reach 6.4 mg/ml in algae. This represents a 100-fold increase in chloroplast expression of ethanol producing enzymes over prior art. This invention contemplates using these technologies in combination for the production of ethanol in photosynthetic algae.

Advantages to the use of algae in particular include 1) the ease of nuclear and chloroplast transformation, 2) the relatively short time between the generation of initial transformants and their scale up to production volumes, 3) the ability to grow phototrophically or heterotrophically, utilizing acetate as a carbon source, 4) the availability of a wide variety of promoters regulated by factors such as light or specific nutrient levels in the medium, 5) the ability to grow cultures on scales ranging from a milli-liters to mega-liters, in a cost effective manner, and 6) the ability of algae grow at a high rate, doubling in cell number in approximately 8 hours via vegetative division with the potential to scale up from 1 liter to 64,000 liter in four to six weeks. Most importantly however, is that this tremendous metabolic potential can be redirected to alcohol production rather than cell growth, potentially with a chemical switch.

Chloroplast targeting multiplies the inherent advantages of using algae. 1) Enzymes encoded in free plastids as well as gene incorporated into the chloroplast genomes have much higher copy numbers than genes encoded in the algal nucleus. In the former case this is simply due to highly copy number replication centers. In the latter case, due the high number of chloroplasts per algae cell. 2) The sequestration of enzymes in an area where the substrate is highly concentrated favors production formation. 3) This sequestration also protects these enzymes away from the hostile cytosolic milieu, where "alien" proteins are often rapidly targeted to lysozome-like and proteosome-like vessicles for proteolytic destruction. 4) placing these enzymes in an environment that favors $CO_2$ dissolution into water so that $CO_2$ produced in the process is routed back to rubisco for incorporation into subsequent ethanol molecules.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

What is claimed is:

1. A method for producing an alcohol in a transgenic eukaryotic algae cell, the method comprising the steps of:
    transforming the algae cell with a DNA construct comprising:
        a DNA sequence comprising a nucleic acid sequence encoding an alcohol producing enzyme, wherein said enzyme comprises pyruvate decarboxylase (PDC);
        a nucleic acid sequence encoding a chloroplast transit peptide (CTP) arranged to be translated in conjunction with the enzyme, wherein said CTP has at least 90% homology to SEQ ID NO:6 or SEQ ID NO:7, or at least 90% homology to a CTP from SEQ ID NOs: 11-20 and 22-27;
        a nucleotide regulatory element that controls expression of the enzyme and chloroplast transit peptide in the algae;
    expressing the alcohol producing enzyme in the algae cell, wherein the enzyme is targeted to the chloroplast by the encoded chloroplast transit peptide; and
    producing the alcohol.

2. The method of claim 1, wherein the alcohol is ethanol.

3. The method of claim 2, wherein the alcohol is methanol and the enzyme is formate dehydrogenase ($F_{ate}$DH), formaldehyde dehydrogenase ($F_{ald}DH$), alcohol dehydrogenase (ADH), or a combination thereof.

4. The method of claim 2, wherein the DNA construct further comprises a nucleic acid sequence encoding alcohol dehydrogenase (ADH).

5. The method of claim 2, wherein the alcohol is butanol and the enzyme is pyruvate-ferredoxin oxidoreductase, acetyl-CoA-acetyl transferase, hydroxybutyryl-CoA dehydrogenase, Crotonase, butyryl CoA dehydrogenase, phosphobutyrylase, butyrate kinase, or a combination thereof.

6. The method of claim 1, wherein the alcohol producing enzyme is translocated to and expressed in the chloroplast.

7. The method of claim 1, wherein the DNA construct further comprises a 3'-nontranslated regulatory sequence.

8. The method of claim 1, wherein the chloroplast transit peptide is SEQ ID NO:6 or SEQ ID NO:7.

9. A method for producing an alcohol in a transgenic eukaryotic algae cell, the method comprising the steps of:
   transforming a chloroplast genome of the algae cell with a DNA construct comprising:
   a DNA sequence comprising a nucleic acid sequence encoding an alcohol producing enzyme, wherein said enzyme comprises pyruvate decarboxylase (PDC);
   a nucleotide regulatory element that controls expression of the enzyme in the algae operably linked to the nucleic acid sequence encoding the alcohol producing enzyme;
   expressing the alcohol producing enzyme in the chloroplast; and
   producing the alcohol.

10. The method of claim 9, wherein the DNA construct further comprises nucleic acid sequences that specify integration of the DNA construct into the chloroplast genome.

11. The method of claim 10, wherein the nucleic acid sequences that specify integration of the DNA construct into the chloroplast genome comprise two regions of homology to the chloroplast genome that flank the nucleic acid sequence encoding the alcohol producing enzyme.

12. The method of claim 11, wherein the DNA construct is integrated into the chloroplast genome by homologous recombination.

13. The method of claim 9, wherein the DNA construct further comprises a chloroplast targeting sequence for integrating the alcohol producing enzyme into the chloroplast genome.

14. The method of claim 13, wherein the chloroplast targeting sequence is selected from the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, or thioredoxin F.

15. The method of claim 9, wherein the alcohol is ethanol.

* * * * *

SEQUENCE LISTING

```
<160> NUMBER OF SEQ ID NOS: 27

<210> SEQ ID NO 1
<211> LENGTH: 392
<212> TYPE: PRT
<213> ORGANISM: Clostridium acetobutylicum

<400> SEQUENCE: 1

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60
```

-continued

```
Pro Ala Arg Gln Ala Ser Phe Lys Ala Gly Leu Pro Val Glu Ile Pro
 65                  70                  75                  80

Ala Met Thr Ile Asn Lys Val Cys Gly Ser Gly Leu Arg Thr Val Ser
                 85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
370                 375                 380

Thr Ala Ile Leu Leu Glu Lys Cys
385                 390

<210> SEQ ID NO 2
<211> LENGTH: 282
<212> TYPE: PRT
<213> ORGANISM: Clostridium acetobutylicum

<400> SEQUENCE: 2

Met Lys Lys Val Cys Val Ile Gly Ala Gly Thr Met Gly Ser Gly Ile
  1               5                  10                  15

Ala Gln Ala Phe Ala Ala Lys Gly Phe Glu Val Val Leu Arg Asp Ile
                 20                  25                  30

Lys Asp Glu Phe Val Asp Arg Gly Leu Asp Phe Ile Asn Lys Asn Leu
             35                  40                  45
```

Ser Lys Leu Val Lys Lys Gly Lys Ile Glu Glu Ala Thr Lys Val Glu
 50                  55                  60

Ile Leu Thr Arg Ile Ser Gly Thr Val Asp Leu Asn Met Ala Ala Asp
 65                  70                  75                  80

Cys Asp Leu Val Ile Glu Ala Ala Val Glu Arg Met Asp Ile Lys Lys
                 85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
            115                 120                 125

Lys Arg Pro Asp Lys Val Ile Gly Met His Phe Phe Asn Pro Ala Pro
130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
                180                 185                 190

Pro Met Ile Asn Glu Ala Val Gly Ile Leu Ala Glu Gly Ile Ala Ser
            195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
            275                 280

<210> SEQ ID NO 3
<211> LENGTH: 258
<212> TYPE: PRT
<213> ORGANISM: Clostridium perfringens

<400> SEQUENCE: 3

Met Glu Asn Ile Ile Phe Asn Glu Ser Asn Gly Ile Ala Glu Val Ile
 1               5                  10                  15

Ile Asn Arg Pro Lys Ala Leu Asn Ala Leu Asn Asn Gln Thr Ile Thr
                20                  25                  30

Glu Leu Gly Glu Val Ile Asn Glu Ile Ser Lys Arg Lys Asp Ile Lys
            35                  40                  45

Thr Val Ile Ile Thr Gly Ala Gly Glu Lys Ala Phe Val Ala Gly Ala
 50                  55                  60

Asp Ile Val Glu Met Lys Asp Leu Asn Ser Met Glu Ala Arg Asp Phe
 65                  70                  75                  80

Ser Arg Leu Ala Gln Lys Val Phe Ser Asp Ile Glu Asn Met Pro Gln
                 85                  90                  95

Ile Val Ile Ala Ala Val Asn Gly Tyr Ala Leu Gly Gly Gly Cys Glu
            100                 105                 110

Leu Ser Met Ala Cys Asp Ile Arg Leu Ala Ser Lys Lys Ala Lys Phe
            115                 120                 125

Gly Gln Pro Glu Val Asn Leu Gly Ile Leu Pro Gly Phe Ala Gly Thr

```
            130                 135                 140
Gln Arg Leu Pro Arg Leu Val Gly Lys Gly Ile Ala Lys Glu Leu Ile
145                 150                 155                 160

Phe Ser Thr Asp Met Ile Asp Ala Glu Glu Ala His Arg Ile Gly Leu
                165                 170                 175

Ala Asn Lys Val Tyr Glu Pro Glu Glu Leu Met Asp Lys Ala Arg Glu
            180                 185                 190

Leu Ala Asn Lys Ile Met Ser Lys Ser Pro Val Gly Val Arg Leu Ala
                195                 200                 205

Lys Ala Ala Ile Asn Asn Gly Leu Asn Met Asp Thr Glu Ser Ala Tyr
            210                 215                 220

Asn Tyr Glu Ala Asp Leu Phe Ala Leu Cys Phe Ser Thr Glu Asp Gln
225                 230                 235                 240

Leu Glu Gly Met Asn Ala Phe Val Asp Lys Arg Lys Ala Asp Phe Lys
                245                 250                 255

Asp Lys

<210> SEQ ID NO 4
<211> LENGTH: 379
<212> TYPE: PRT
<213> ORGANISM: Clostridium acetobutylicum

<400> SEQUENCE: 4

Met Asp Phe Asn Leu Thr Arg Glu Gln Glu Leu Val Arg Gln Met Val
1               5                   10                  15

Arg Glu Phe Ala Glu Asn Glu Val Lys Pro Ile Ala Ala Glu Ile Asp
            20                  25                  30

Glu Thr Glu Arg Phe Pro Met Glu Asn Val Lys Lys Met Gly Gln Tyr
        35                  40                  45

Gly Met Met Gly Ile Pro Phe Ser Lys Glu Tyr Gly Gly Ala Gly Gly
    50                  55                  60

Asp Val Leu Ser Tyr Ile Ile Ala Val Glu Glu Leu Ser Lys Val Cys
65                  70                  75                  80

Gly Thr Thr Gly Val Ile Leu Ser Ala His Thr Ser Leu Cys Ala Ser
                85                  90                  95

Leu Ile Asn Glu His Gly Thr Glu Glu Gln Lys Gln Lys Tyr Leu Val
            100                 105                 110

Pro Leu Ala Lys Gly Glu Lys Ile Gly Ala Tyr Gly Leu Thr Glu Pro
        115                 120                 125

Asn Ala Gly Thr Asp Ser Gly Ala Gln Gln Thr Val Ala Val Leu Glu
    130                 135                 140

Gly Asp His Tyr Val Ile Asn Gly Ser Lys Ile Phe Ile Thr Asn Gly
145                 150                 155                 160

Gly Val Ala Asp Thr Phe Val Ile Phe Ala Met Thr Asp Arg Thr Lys
                165                 170                 175

Gly Thr Lys Gly Ile Ser Ala Phe Ile Ile Glu Lys Gly Phe Lys Gly
            180                 185                 190

Phe Ser Ile Gly Lys Val Glu Gln Lys Leu Gly Ile Arg Ala Ser Ser
        195                 200                 205

Thr Thr Glu Leu Val Phe Glu Asp Met Ile Val Pro Val Glu Asn Met
    210                 215                 220

Ile Gly Lys Glu Gly Lys Gly Phe Pro Ile Ala Met Lys Thr Leu Asp
225                 230                 235                 240

Gly Gly Arg Ile Gly Ile Ala Ala Gln Ala Leu Gly Ile Ala Glu Gly
```

```
                    245                 250                 255
Ala Phe Asn Glu Ala Arg Ala Tyr Met Lys Glu Arg Lys Gln Phe Gly
                260                 265                 270

Arg Ser Leu Asp Lys Phe Gln Gly Leu Ala Trp Met Met Ala Asp Met
            275                 280                 285

Asp Val Ala Ile Glu Ser Ala Arg Tyr Leu Val Tyr Lys Ala Ala Tyr
        290                 295                 300

Leu Lys Gln Ala Gly Leu Pro Tyr Thr Val Asp Ala Ala Arg Ala Lys
305                 310                 315                 320

Leu His Ala Ala Asn Val Ala Met Asp Val Thr Thr Lys Ala Val Gln
                325                 330                 335

Leu Phe Gly Gly Tyr Gly Tyr Thr Lys Asp Tyr Pro Val Glu Arg Met
                340                 345                 350

Met Arg Asp Ala Lys Ile Thr Glu Ile Tyr Glu Gly Thr Ser Glu Val
                355                 360                 365

Gln Lys Leu Val Ile Ser Gly Lys Ile Phe Arg
                370                 375

<210> SEQ ID NO 5
<211> LENGTH: 355
<212> TYPE: PRT
<213> ORGANISM: Clostridium acetobutylicum

<400> SEQUENCE: 5

Met Tyr Arg Leu Leu Ile Ile Asn Pro Gly Ser Thr Ser Thr Lys Ile
1               5                   10                  15

Gly Ile Tyr Asp Asp Glu Lys Glu Ile Phe Glu Lys Thr Leu Arg His
                20                  25                  30

Ser Ala Glu Glu Ile Glu Lys Tyr Asn Thr Ile Phe Asp Gln Phe Gln
            35                  40                  45

Phe Arg Lys Asn Val Ile Leu Asp Ala Leu Lys Glu Ala Asn Ile Glu
        50                  55                  60

Val Ser Ser Leu Asn Ala Val Val Gly Arg Gly Gly Leu Leu Lys Pro
65                  70                  75                  80

Ile Val Ser Gly Thr Tyr Ala Val Asn Gln Lys Met Leu Glu Asp Leu
                85                  90                  95

Lys Val Gly Val Gln Gly Gln His Ala Ser Asn Leu Gly Gly Ile Ile
            100                 105                 110

Ala Asn Glu Ile Ala Lys Glu Ile Asn Val Pro Ala Tyr Ile Val Asp
        115                 120                 125

Pro Val Val Val Asp Glu Leu Asp Glu Val Ser Arg Ile Ser Gly Met
    130                 135                 140

Ala Asp Ile Pro Arg Lys Ser Ile Phe His Ala Leu Asn Gln Lys Ala
145                 150                 155                 160

Val Ala Arg Arg Tyr Ala Lys Glu Val Gly Lys Lys Tyr Glu Asp Leu
                165                 170                 175

Asn Leu Ile Val Val His Met Gly Gly Gly Thr Ser Val Gly Thr His
            180                 185                 190

Lys Asp Gly Arg Val Ile Glu Val Asn Asn Thr Leu Asp Gly Glu Gly
        195                 200                 205

Pro Phe Ser Pro Glu Arg Ser Gly Gly Val Pro Ile Gly Asp Leu Val
    210                 215                 220

Arg Leu Cys Phe Ser Asn Lys Tyr Thr Tyr Glu Glu Val Met Lys Lys
225                 230                 235                 240
```

```
Ile Asn Gly Lys Gly Gly Val Val Ser Tyr Leu Asn Thr Ile Asp Phe
                245                 250                 255

Lys Ala Val Val Asp Lys Ala Leu Glu Gly Asp Lys Lys Cys Ala Leu
            260                 265                 270

Ile Tyr Glu Ala Phe Thr Phe Gln Val Ala Lys Glu Ile Gly Lys Cys
        275                 280                 285

Ser Thr Val Leu Lys Gly Asn Val Asp Ala Ile Ile Leu Thr Gly Gly
    290                 295                 300

Ile Ala Tyr Asn Glu His Val Cys Asn Ala Ile Glu Asp Arg Val Lys
305                 310                 315                 320

Phe Ile Ala Pro Val Val Arg Tyr Gly Gly Glu Asp Glu Leu Leu Ala
                325                 330                 335

Leu Ala Glu Gly Gly Leu Arg Val Leu Arg Gly Glu Lys Ala Lys
            340                 345                 350

Glu Tyr Lys
        355

<210> SEQ ID NO 6
<211> LENGTH: 27
<212> TYPE: PRT
<213> ORGANISM: Chlamydomonas reinhardtii

<400> SEQUENCE: 6

Met Lys Ser Ser Ala Val Ser Ala Gly Gln Arg Val Gly Gly Ala Arg
1               5                   10                  15

Val Ala Thr Arg Ser Val Arg Arg Ala Gln Leu
            20                  25

<210> SEQ ID NO 7
<211> LENGTH: 23
<212> TYPE: PRT
<213> ORGANISM: Chlamydomonas reinhardtii

<400> SEQUENCE: 7

Met Arg Ser Thr Phe Ala Ala Arg Val Gly Ala Lys Pro Ala Val Arg
1               5                   10                  15

Gly Ala Arg Pro Ala Ser Arg
            20

<210> SEQ ID NO 8
<211> LENGTH: 379
<212> TYPE: PRT
<213> ORGANISM: Artificial Sequence
<220> FEATURE:
<223> OTHER INFORMATION: synthetic polypeptide

<400> SEQUENCE: 8

Met Ser Thr Thr Gly Gln Ile Ile Arg Cys Lys Ala Ala Val Ala Trp
1               5                   10                  15

Glu Ala Gly Lys Pro Leu Val Met Glu Glu Val Glu Val Ala Pro Pro
            20                  25                  30

Gln Lys His Glu Val Arg Ile Lys Ile Leu Phe Thr Ser Leu Cys His
        35                  40                  45

Thr Asp Val Tyr Phe Trp Glu Ala Lys Gly Gln Thr Pro Leu Phe Pro
    50                  55                  60

Arg Ile Phe Gly His Glu Ala Gly Gly Ile Val Glu Ser Val Gly Glu
65                  70                  75                  80

Gly Val Thr Asp Leu Gln Pro Gly Asp His Val Leu Pro Ile Phe Thr
                85                  90                  95
```

```
Gly Glu Cys Gly Asp Cys Phe His Cys His Ser Glu Ser Asn Met
                100                 105                 110
Cys Asp Leu Leu Arg Ile Asn Thr Glu Arg Gly Met Ile His Asp
            115                 120                 125
Gly Glu Ser Arg Phe Ser Ile Asn Gly Lys Pro Ile His His Phe Leu
    130                 135                 140
Gly Thr Ser Thr Phe Ser Glu Tyr Thr Val Val His Ser Gly Gln Val
145                 150                 155                 160
Ala Lys Ile Asn Pro Asp Ala Pro Leu Asp Lys Val Cys Ile Val Ser
                165                 170                 175
Cys Gly Leu Ser Thr Gly Leu Gly Ala Thr Leu Asn Val Ala Lys Pro
            180                 185                 190
Pro Arg Gly Gln Ser Val Ala Ile Phe Gly Leu Gly Ala Val Gly Leu
        195                 200                 205
Ala Ala Ala Glu Gly Ala Arg Ile Ala Gly Ala Ser Arg Ile Ile Gly
    210                 215                 220
Val Asp Leu Asn Ser Gln Arg Phe Ala Gln Ala Lys Glu Phe Gly Val
225                 230                 235                 240
Thr Glu Phe Val Asn Pro Arg Asp His Gly Lys Pro Val Gln Gln Val
                245                 250                 255
Ile Ala Glu Met Thr Asn Gly Gly Val Asp Arg Ser Val Glu Cys Thr
            260                 265                 270
Gly Ser Val Gln Ala Met Ile Gln Ala Phe Glu Cys Val His Asp Gly
        275                 280                 285
Trp Gly Val Ala Val Leu Val Gly Val Pro Ser Lys Asp Asp Ala Phe
    290                 295                 300
Glu Thr His Pro Met Asn Phe Leu Asn Glu Arg Thr Leu Lys Gly Thr
305                 310                 315                 320
Phe Phe Gly Asn Tyr Lys Pro Lys Thr Asp Ile Pro Gly Val Val Glu
                325                 330                 335
Lys Tyr Met Asn Lys Glu Leu Glu Leu Glu Lys Phe Ile Thr His Thr
            340                 345                 350
Val Pro Phe Ser Glu Ile Asn Lys Ala Phe Asp Tyr Met Leu Lys Gly
        355                 360                 365
Glu Ser Ile Arg Cys Ile Ile Thr Met Gly Ala
    370                 375

<210> SEQ ID NO 9
<211> LENGTH: 836
<212> TYPE: PRT
<213> ORGANISM: Artificial Sequence
<220> FEATURE:
<223> OTHER INFORMATION: synthetic polypeptide

<400> SEQUENCE: 9

Met Leu Lys Phe Gln Thr Val Arg Gly Gly Leu Arg Leu Asn Val Arg
1               5                   10                  15
Arg Leu Glu Tyr Lys Pro Ile Lys Lys Val Met Val Ala Asn Gly Glu
            20                  25                  30
Ile Ala Ile Arg Val Phe Arg Ala Cys Thr Glu Leu Gly Ile Arg Thr
        35                  40                  45
Val Ala Val Tyr Ser Glu Gln Asp Thr Gly Gln Met His Arg Gln Lys
    50                  55                  60
Ala Asp Glu Ala Tyr Leu Ile Gly Arg Gly Leu Ala Pro Val Gln Ala
65                  70                  75                  80
```

-continued

Tyr Leu His Ile Pro Asp Ile Ile Lys Val Ala Lys Glu Asn Gly Val
                85                  90                  95
Asp Ala Val His Pro Gly Tyr Gly Phe Leu Ser Glu Arg Ala Asp Phe
            100                 105                 110
Ala Gln Ala Cys Gln Asp Ala Gly Val Arg Phe Ile Gly Pro Ser Pro
        115                 120                 125
Glu Val Val Arg Lys Met Gly Asp Lys Val Glu Ala Arg Ala Ile Ala
    130                 135                 140
Ala Gly Val Pro Val Val Pro Gly Thr Asp Ser Pro Ile Ser Ser Leu
145                 150                 155                 160
His Glu Ala His Glu Phe Ser Asn Thr Phe Gly Phe Pro Ile Ile Phe
                165                 170                 175
Lys Ala Ala Tyr Gly Gly Gly Gly Arg Gly Met Arg Val Val His Ser
            180                 185                 190
Tyr Glu Glu Leu Glu Glu Asn Tyr Thr Ala Tyr Ala Glu Ala Leu Ala
        195                 200                 205
Ala Phe Gly Asn Gly Ala Leu Phe Val Glu Lys Phe Ile Glu Lys Pro
    210                 215                 220
Arg His Ile Glu Val Gln Ile Leu Gly Asp Gln Tyr Gly Asn Ile Leu
225                 230                 235                 240
His Leu Tyr Glu Arg Asp Cys Ser Ile Gln Arg Arg His Gln Lys Val
                245                 250                 255
Val Ala Pro Ala Thr His Leu Asp Pro Gln Leu Arg Ser Arg Leu Thr
            260                 265                 270
Ser Asp Ser Val Lys Leu Ala Lys Gln Val Gly Tyr Glu Asn Ala Gly
        275                 280                 285
Thr Val Glu Phe Leu Val Asp Lys His Gly Lys His Tyr Phe Ile Glu
    290                 295                 300
Val Asn Ser Arg Leu Gln Val Glu His Thr Glu Ile Thr Asp Val
305                 310                 315                 320
Asp Leu Val His Ala Gln Ile His Val Ser Glu Gln Arg Ser Leu Pro
                325                 330                 335
Asp Leu Gly Leu Arg Gln Glu Asn Ile Arg Ile Asn Gly Cys Ala Ile
            340                 345                 350
Gln Cys Arg Val Thr Thr Glu Asp Pro Ala Arg Ser Phe Gln Pro Asp
        355                 360                 365
Thr Arg Ile Glu Val Phe Arg Ser Gly Glu Gly Met Gly Ile Arg Leu
    370                 375                 380
Asp Asn Ala Ser Ala Phe Gln Gly Ala Val Ile Ser Pro His Tyr Asp
385                 390                 395                 400
Ser Leu Leu Val Lys Val Ile Ala His Gly Lys Asp His Pro Thr Ala
                405                 410                 415
Ala Thr Lys Met Ser Arg Ala Leu Ala Glu Phe Arg Val Arg Gly Val
            420                 425                 430
Lys Thr Asn Ile Pro Phe Leu Gln Asn Val Leu Asn Gln Gln Phe
        435                 440                 445
Leu Ala Gly Thr Val Asp Thr Gln Phe Ile Asp Glu Asn Pro Glu Leu
    450                 455                 460
Phe Gln Leu Arg Pro Ala Gln Asn Arg Ala Gln Lys Leu Leu His Tyr
465                 470                 475                 480
Leu Gly His Val Met Val Asn Gly Pro Thr Thr Pro Ile Pro Val Asn
                485                 490                 495

Val Ser Pro Ser Pro Val Asp Pro Ala Val Pro Val Pro Ile Gly
            500                 505                 510

Pro Pro Pro Ala Gly Phe Arg Asp Ile Leu Leu Arg Glu Gly Pro Glu
            515                 520                 525

Gly Phe Ala Arg Ala Val Arg Met His Gln Gly Leu Leu Leu Met Asp
            530                 535                 540

Thr Thr Phe Arg Asp Ala His Gln Ser Leu Leu Ala Thr Arg Val Arg
545                 550                 555                 560

Thr His Asp Leu Lys Lys Ile Ala Pro Tyr Val Ala His Asn Phe Asn
            565                 570                 575

Lys Leu Phe Ser Met Glu Asn Trp Gly Gly Ala Thr Phe Asp Val Ala
            580                 585                 590

Met Arg Phe Leu Tyr Glu Cys Pro Trp Arg Arg Leu Gln Glu Leu Arg
            595                 600                 605

Glu Leu Ile Pro Asn Ile Pro Phe Gln Met Leu Leu Arg Gly Ala Asn
            610                 615                 620

Ala Val Gly Tyr Thr Asn Tyr Pro Asp Asn Val Val Phe Lys Phe Cys
625                 630                 635                 640

Glu Val Ala Lys Glu Asn Gly Met Asp Val Phe Arg Val Phe Asp Ser
            645                 650                 655

Leu Asn Tyr Leu Pro Asn Met Leu Leu Gly Met Glu Ala Ala Gly Ser
            660                 665                 670

Ala Gly Gly Val Val Glu Ala Ala Ile Ser Tyr Thr Gly Asp Val Ala
            675                 680                 685

Asp Pro Ser Arg Thr Lys Tyr Ser Leu Glu Tyr Tyr Met Gly Leu Ala
            690                 695                 700

Glu Glu Leu Val Arg Ala Gly Thr His Ile Leu Cys Ile Lys Asp Met
705                 710                 715                 720

Ala Gly Leu Leu Lys Pro Ala Ala Cys Thr Met Leu Val Ser Ser Leu
            725                 730                 735

Arg Asp Arg Phe Pro Asp Leu Pro Leu His Ile His Thr His Asp Thr
            740                 745                 750

Ser Gly Ala Gly Val Ala Ala Met Leu Ala Cys Ala Gln Ala Gly Ala
            755                 760                 765

Asp Val Val Asp Val Ala Val Asp Ser Met Ser Gly Met Thr Ser Gln
            770                 775                 780

Pro Ser Met Gly Ala Leu Val Ala Cys Thr Lys Gly Thr Pro Leu Asp
785                 790                 795                 800

Thr Glu Val Pro Leu Glu Arg Val Phe Asp Tyr Ser Glu Tyr Trp Glu
            805                 810                 815

Gly Ala Arg Gly Leu Tyr Ala Ala Phe Asp Cys Thr Ala Thr Met Lys
            820                 825                 830

Ser Gly Asn Ser
        835

<210> SEQ ID NO 10
<211> LENGTH: 64
<212> TYPE: DNA
<213> ORGANISM: Artificial Sequence
<220> FEATURE:
<223> OTHER INFORMATION: synthetic oligonucleotide

<400> SEQUENCE: 10
taatatagac taaaaacctt tttaatctac tggtccacca tctaaaatta aaccatttta    60
gatg    64

```
<210> SEQ ID NO 11
<211> LENGTH: 383
<212> TYPE: PRT
<213> ORGANISM: Spinacia oleracea

<400> SEQUENCE: 11

Met Ala Ser Leu Val Asn Asn Ala Tyr Ala Ala Leu Arg Thr Ser Lys
1               5                   10                  15

Leu Glu Leu Arg Glu Val Lys Asn Leu Ala Asn Phe Arg Val Gly Pro
            20                  25                  30

Pro Ser Ser Leu Ser Cys Asn Asn Phe Lys Lys Val Ser Ser Ser Pro
        35                  40                  45

Ile Thr Cys Lys Ala Val Ser Leu Ser Pro Pro Ser Thr Ile Glu Gly
    50                  55                  60

Leu Asn Ile Ala Glu Asp Val Ser Gln Leu Ile Gly Lys Thr Pro Met
65                  70                  75                  80

Val Tyr Leu Asn Asn Val Ser Lys Gly Ser Val Ala Asn Ile Ala Ala
                85                  90                  95

Lys Leu Glu Ser Met Glu Pro Cys Cys Ser Val Lys Asp Arg Ile Gly
            100                 105                 110

Tyr Ser Met Ile Asp Asp Ala Glu Gln Lys Gly Val Ile Thr Pro Gly
        115                 120                 125

Lys Thr Thr Leu Val Glu Pro Thr Ser Gly Asn Thr Gly Ile Gly Leu
    130                 135                 140

Ala Phe Ile Ala Ala Arg Gly Tyr Lys Ile Thr Leu Thr Met Pro
145                 150                 155                 160

Ala Ser Met Ser Met Glu Arg Arg Val Ile Leu Lys Ala Phe Gly Ala
                165                 170                 175

Glu Leu Val Leu Thr Asp Pro Ala Lys Gly Met Lys Gly Ala Val Glu
            180                 185                 190

Lys Ala Glu Glu Ile Leu Lys Lys Thr Pro Asp Ser Tyr Met Leu Gln
        195                 200                 205

Gln Phe Asp Asn Pro Ala Asn Pro Lys Ile His Tyr Glu Thr Thr Gly
    210                 215                 220

Pro Glu Ile Trp Glu Asp Thr Lys Gly Lys Val Asp Ile Phe Val Ala
225                 230                 235                 240

Gly Ile Gly Thr Gly Gly Thr Ile Ser Gly Val Gly Arg Tyr Leu Lys
                245                 250                 255

Glu Arg Asn Pro Gly Val Gln Val Ile Gly Ile Glu Pro Thr Glu Ser
            260                 265                 270

Asn Ile Leu Ser Gly Gly Lys Pro Gly Pro His Lys Ile Gln Gly Leu
        275                 280                 285

Gly Ala Gly Phe Val Pro Ser Asn Leu Asp Leu Gly Val Met Asp Glu
    290                 295                 300

Val Ile Glu Val Ser Ser Glu Glu Ala Val Glu Met Ala Lys Gln Leu
305                 310                 315                 320

Ala Met Lys Glu Gly Leu Leu Val Gly Ile Ser Ser Gly Ala Ala Ala
                325                 330                 335

Ala Ala Ala Val Arg Ile Gly Lys Arg Pro Glu Asn Ala Gly Lys Leu
            340                 345                 350

Ile Ala Val Val Phe Pro Ser Phe Gly Glu Arg Tyr Leu Ser Ser Ile
        355                 360                 365

Leu Phe Gln Ser Ile Arg Glu Glu Cys Glu Asn Met Lys Pro Glu
```

370                 375                 380

<210> SEQ ID NO 12
<211> LENGTH: 573
<212> TYPE: PRT
<213> ORGANISM: Glycine max

<400> SEQUENCE: 12

Met Thr Thr Ser Phe Gly Pro Ala Thr Thr Ser Ala Pro Leu Lys Asp
1               5                   10                  15

His Lys Val Gln Ile Pro Ser Phe His Gly Leu Arg Ser Ser Ser Ala
            20                  25                  30

Ser Ala Leu Pro Arg Asn Ala Leu Ser Leu Pro Ser Ser Thr Arg Ser
        35                  40                  45

Leu Ser Leu Ile Arg Ala Val Ser Thr Pro Ala Gln Ser Glu Thr Ala
    50                  55                  60

Thr Val Lys Arg Ser Lys Val Glu Ile Phe Lys Glu Gln Ser Asn Phe
65                  70                  75                  80

Ile Arg Tyr Pro Leu Asn Glu Asp Ile Leu Thr Asp Ala Pro Asn Ile
                85                  90                  95

Ser Glu Ala Ala Thr Gln Leu Ile Lys Phe His Gly Ser Tyr Gln Gln
            100                 105                 110

Tyr Asn Arg Glu Glu Arg Gly Ser Arg Ser Tyr Ser Phe Met Ile Arg
        115                 120                 125

Thr Lys Asn Pro Cys Gly Lys Val Ser Asn Gln Leu Tyr Leu Thr Met
    130                 135                 140

Asp Asp Leu Ala Asp Gln Phe Gly Ile Gly Thr Leu Arg Leu Thr Thr
145                 150                 155                 160

Arg Gln Thr Phe Gln Leu His Gly Val Leu Lys Lys Asp Leu Lys Thr
                165                 170                 175

Val Met Gly Thr Ile Ile Arg Asn Met Gly Ser Thr Leu Gly Ala Cys
            180                 185                 190

Gly Asp Leu Asn Arg Asn Val Leu Ala Pro Ala Ala Pro Leu Ala Arg
        195                 200                 205

Lys Asp Tyr Leu Phe Ala Gln Gln Thr Ala Glu Asn Ile Ala Ala Leu
    210                 215                 220

Leu Ala Pro Gln Ser Gly Phe Tyr Tyr Asp Ile Trp Val Asp Gly Glu
225                 230                 235                 240

Lys Ile Leu Thr Ser Glu Pro Pro Glu Val Val Gln Ala Arg Asn Asp
                245                 250                 255

Asn Ser His Gly Thr Asn Phe Pro Asp Ser Pro Glu Pro Ile Tyr Gly
            260                 265                 270

Thr Gln Phe Leu Pro Arg Lys Phe Lys Ile Ala Val Thr Val Pro Thr
        275                 280                 285

Asp Asn Ser Val Asp Ile Leu Thr Asn Asp Ile Gly Val Val Val Val
    290                 295                 300

Thr Asp Asp Asp Gly Glu Pro Gln Gly Phe Asn Ile Tyr Val Gly Gly
305                 310                 315                 320

Gly Met Gly Arg Thr His Arg Leu Glu Thr Thr Phe Pro Arg Leu Ala
                325                 330                 335

Glu Pro Ile Gly Tyr Val Pro Lys Glu Asp Ile Leu Tyr Ala Val Lys
            340                 345                 350

Ala Ile Val Val Thr Gln Arg Glu Asn Gly Arg Arg Asp Asp Arg Lys
        355                 360                 365

```
Tyr Ser Arg Leu Lys Tyr Leu Ile Ser Ser Trp Gly Ile Glu Lys Phe
    370                 375                 380

Arg Ser Val Val Glu Gln Tyr Tyr Gly Lys Lys Phe Glu Pro Phe Arg
385                 390                 395                 400

Ala Leu Pro Glu Trp Glu Phe Lys Ser Tyr Leu Gly Trp His Glu Gln
                405                 410                 415

Gly Asp Gly Lys Leu Phe Tyr Gly Leu His Val Asp Asn Gly Arg Ile
                420                 425                 430

Gly Gly Asn Met Lys Lys Thr Leu Arg Glu Val Ile Glu Lys Tyr Asn
            435                 440                 445

Leu Asn Val Arg Ile Thr Pro Asn Gln Asn Ile Ile Leu Thr Asp Val
450                 455                 460

Arg Ala Ala Trp Lys Arg Pro Ile Thr Thr Leu Ala Gln Ala Gly
465                 470                 475                 480

Leu Leu Gln Pro Arg Phe Val Asp Pro Leu Asn Ile Thr Ala Met Ala
                485                 490                 495

Cys Pro Ala Phe Pro Leu Cys Pro Leu Ala Ile Thr Gly Ala Glu Arg
            500                 505                 510

Gly Ile Pro Asn Ile Leu Lys Arg Ile Arg Asp Val Phe Asp Lys Val
            515                 520                 525

Gly Leu Lys Tyr Ser Glu Ser Val Val Arg Ile Thr Gly Cys Pro
    530                 535                 540

Asn Gly Cys Ala Arg Pro Tyr Met Ala Glu Leu Gly Leu Val Gly Asp
545                 550                 555                 560

Gly Pro Asn Ser Tyr Gln Ile Trp Leu Gly Gly Thr Pro
                565                 570

<210> SEQ ID NO 13
<211> LENGTH: 328
<212> TYPE: PRT
<213> ORGANISM: Pisum sativum

<400> SEQUENCE: 13

Met Ser Thr Ser Ser Ile Asn Gly Phe Ser Leu Ser Ser Leu Ser Pro
1               5                   10                  15

Ala Lys Thr Ser Thr Lys Arg Thr Thr Leu Arg Pro Phe Val Ser Ala
                20                  25                  30

Ser Leu Asn Thr Ser Ser Ser Ser Ser Ser Thr Phe Pro Ser Leu
            35                  40                  45

Ile Gln Asp Lys Pro Val Phe Ala Ser Ser Pro Ile Ile Thr Pro
50                  55                  60

Val Leu Arg Glu Glu Met Gly Lys Gly Tyr Asp Glu Ala Ile Glu Glu
65                  70                  75                  80

Leu Gln Lys Leu Leu Arg Glu Lys Thr Glu Leu Lys Ala Thr Ala Ala
                85                  90                  95

Glu Lys Val Glu Gln Ile Thr Ala Gln Leu Gly Thr Thr Ser Ser Ser
                100                 105                 110

Asp Gly Ile Pro Lys Ser Glu Ala Ser Glu Arg Ile Lys Thr Gly Phe
            115                 120                 125

Leu His Phe Lys Lys Glu Lys Tyr Asp Lys Asn Pro Ala Leu Tyr Gly
    130                 135                 140

Glu Leu Ala Lys Gly Gln Ser Pro Pro Phe Met Val Phe Ala Cys Ser
145                 150                 155                 160

Asp Ser Arg Val Cys Pro Ser His Val Leu Asp Phe Gln Pro Gly Glu
                165                 170                 175
```

```
Ala Phe Val Val Arg Asn Val Ala Asn Leu Val Pro Pro Tyr Asp Gln
            180                 185                 190

Ala Lys Tyr Ala Gly Thr Gly Ala Ile Glu Tyr Ala Val Leu His
        195                 200                 205

Leu Lys Val Ser Asn Ile Val Val Ile Gly His Ser Ala Cys Gly Gly
    210                 215                 220

Ile Lys Gly Leu Leu Ser Phe Pro Phe Asp Gly Thr Tyr Ser Thr Asp
225                 230                 235                 240

Phe Ile Glu Glu Trp Val Lys Ile Gly Leu Pro Ala Lys Ala Lys Val
                245                 250                 255

Lys Ala Gln His Gly Asp Ala Pro Phe Ala Glu Leu Cys Thr His Cys
            260                 265                 270

Glu Lys Glu Ala Val Asn Ala Ser Leu Gly Asn Leu Leu Thr Tyr Pro
        275                 280                 285

Phe Val Arg Glu Gly Leu Val Asn Lys Thr Leu Ala Leu Lys Gly Gly
    290                 295                 300

Tyr Tyr Asp Phe Val Lys Gly Ser Phe Glu Leu Trp Gly Leu Glu Phe
305                 310                 315                 320

Gly Leu Ser Ser Thr Phe Ser Val
                325

<210> SEQ ID NO 14
<211> LENGTH: 413
<212> TYPE: PRT
<213> ORGANISM: Nicotiana tabacum

<400> SEQUENCE: 14

Met Ala Thr Ile Ser Asn Pro Ala Glu Ile Ala Ala Ser Ser Pro Ser
1               5                   10                  15

Phe Ala Phe Tyr His Ser Ser Phe Ile Pro Lys Gln Cys Cys Phe Thr
                20                  25                  30

Lys Ala Arg Arg Lys Ser Leu Cys Lys Pro Gln Arg Phe Ser Ile Ser
            35                  40                  45

Ser Ser Phe Thr Pro Phe Asp Ser Ala Lys Ile Lys Val Ile Gly Val
50                  55                  60

Gly Gly Gly Gly Asn Asn Ala Val Asn Arg Met Ile Gly Ser Gly Leu
65                  70                  75                  80

Gln Gly Val Asp Phe Tyr Ala Ile Asn Thr Asp Ala Gln Ala Leu Leu
                85                  90                  95

Gln Ser Ala Ala Glu Asn Pro Leu Gln Ile Gly Glu Leu Leu Thr Arg
            100                 105                 110

Gly Leu Gly Thr Gly Gly Asn Pro Leu Leu Gly Glu Gln Ala Ala Glu
        115                 120                 125

Glu Ser Lys Glu Ala Ile Ala Asn Ser Leu Lys Gly Ser Asp Met Val
130                 135                 140

Phe Ile Thr Ala Gly Met Gly Gly Gly Thr Gly Ser Gly Ala Ala Pro
145                 150                 155                 160

Val Val Ala Gln Ile Ala Lys Glu Ala Gly Tyr Leu Thr Val Gly Val
                165                 170                 175

Val Thr Tyr Pro Phe Ser Phe Glu Gly Arg Lys Arg Ser Val Gln Ala
            180                 185                 190

Leu Glu Ala Ile Glu Lys Leu Gln Lys Asn Val Asp Thr Leu Ile Val
        195                 200                 205

Ile Pro Asn Asp Arg Leu Leu Asp Ile Ala Asp Glu Gln Thr Pro Leu
```

```
                    210                 215                 220
Gln Asp Ala Phe Leu Leu Ala Asp Asp Val Leu Arg Gln Gly Val Gln
225                 230                 235                 240

Gly Ile Ser Asp Ile Ile Thr Ile Pro Gly Leu Val Asn Val Asp Phe
                245                 250                 255

Ala Asp Val Lys Ala Val Met Lys Asp Ser Gly Thr Ala Met Leu Gly
                260                 265                 270

Val Gly Val Ser Ser Lys Asn Arg Ala Glu Glu Ala Ala Glu Gln
                275                 280                 285

Ala Thr Leu Ala Pro Leu Ile Gly Ser Ser Ile Gln Ser Ala Thr Gly
290                 295                 300

Val Val Tyr Asn Ile Thr Gly Gly Lys Asp Ile Thr Leu Gln Glu Val
305                 310                 315                 320

Asn Arg Val Ser Gln Val Val Thr Ser Leu Ala Asp Pro Ser Ala Asn
                325                 330                 335

Ile Ile Phe Gly Ala Val Asp Glu Arg Tyr Asn Gly Glu Ile His
                340                 345                 350

Val Thr Ile Ile Ala Thr Gly Phe Thr Gln Ser Phe Gln Lys Thr Leu
                355                 360                 365

Leu Ser Asp Pro Arg Gly Ala Lys Leu Ala Asp Lys Gly Pro Val Ile
370                 375                 380

Gln Glu Ser Met Ala Ser Pro Val Thr Leu Arg Ser Ser Thr Ser Pro
385                 390                 395                 400

Ser Thr Thr Ser Arg Thr Pro Thr Arg Arg Leu Phe Phe
                405                 410

<210> SEQ ID NO 15
<211> LENGTH: 328
<212> TYPE: PRT
<213> ORGANISM: Pisum sativum

<400> SEQUENCE: 15

Met Ser Thr Ser Ser Ile Asn Gly Phe Ser Leu Ser Ser Leu Ser Pro
1               5                   10                  15

Ala Lys Thr Ser Thr Lys Arg Thr Thr Leu Arg Pro Phe Val Ser Ala
                20                  25                  30

Ser Leu Asn Thr Ser Ser Ser Ser Ser Ser Thr Phe Pro Ser Leu
                35                  40                  45

Ile Gln Asp Lys Pro Val Phe Ala Ser Ser Pro Ile Ile Thr Pro
50                  55                  60

Val Leu Arg Glu Glu Met Gly Lys Gly Tyr Asp Glu Ala Ile Glu Glu
65                  70                  75                  80

Leu Gln Lys Leu Leu Arg Glu Lys Thr Glu Leu Lys Ala Thr Ala Ala
                85                  90                  95

Glu Lys Val Glu Gln Ile Thr Ala Gln Leu Gly Thr Thr Ser Ser Ser
                100                 105                 110

Asp Gly Ile Pro Lys Ser Glu Ala Ser Glu Arg Ile Lys Thr Gly Phe
                115                 120                 125

Leu His Phe Lys Lys Glu Lys Tyr Asp Lys Asn Pro Ala Leu Tyr Gly
                130                 135                 140

Glu Leu Ala Lys Gly Gln Ser Pro Pro Phe Met Val Phe Ala Cys Ser
145                 150                 155                 160

Asp Ser Arg Val Cys Pro Ser His Val Leu Asp Phe Gln Pro Gly Glu
                165                 170                 175
```

```
Ala Phe Val Val Arg Asn Val Ala Asn Leu Val Pro Pro Tyr Asp Gln
            180                 185                 190

Ala Lys Tyr Ala Gly Thr Gly Ala Ala Ile Glu Tyr Ala Val Leu His
            195                 200                 205

Leu Lys Val Ser Asn Ile Val Val Ile Gly His Ser Ala Cys Gly Gly
            210                 215                 220

Ile Lys Gly Leu Leu Ser Phe Pro Phe Asp Gly Thr Tyr Ser Thr Asp
225                 230                 235                 240

Phe Ile Glu Glu Trp Val Lys Ile Gly Leu Pro Ala Lys Ala Lys Val
            245                 250                 255

Lys Ala Gln His Gly Asp Ala Pro Phe Ala Glu Leu Cys Thr His Cys
            260                 265                 270

Glu Lys Glu Ala Val Asn Ala Ser Leu Gly Asn Leu Leu Thr Tyr Pro
            275                 280                 285

Phe Val Arg Glu Gly Leu Val Asn Lys Thr Leu Ala Leu Lys Gly Gly
            290                 295                 300

Tyr Tyr Asp Phe Val Lys Gly Ser Phe Glu Leu Trp Gly Leu Glu Phe
305                 310                 315                 320

Gly Leu Ser Ser Thr Phe Ser Val
            325

<210> SEQ ID NO 16
<211> LENGTH: 299
<212> TYPE: PRT
<213> ORGANISM: Arabidopsis thaliana

<400> SEQUENCE: 16

Met Ala Ser Leu Leu Arg Pro Thr Pro Leu Leu Ser Thr Pro Arg Lys
1               5                   10                  15

Leu Thr His Ser His Leu His Thr Ser Ile Ser Phe Pro Phe Gln Ile
            20                  25                  30

Ser Thr Gln Arg Lys Pro Gln Lys His Leu Leu Asn Leu Cys Arg Ser
        35                  40                  45

Thr Pro Thr Pro Ser Gln Gln Lys Ala Ser Gln Arg Lys Arg Thr Arg
    50                  55                  60

Tyr Arg Lys Gln Tyr Pro Gly Glu Asn Ile Gly Ile Thr Glu Glu Met
65                  70                  75                  80

Arg Phe Val Ala Met Arg Leu Arg Asn Val Asn Gly Lys Lys Leu Asp
                85                  90                  95

Leu Ser Glu Asp Lys Thr Asp Thr Glu Lys Glu Glu Glu Glu Glu Glu
            100                 105                 110

Glu Asp Asp Asp Asp Asp Glu Val Lys Glu Glu Thr Trp Lys Pro
            115                 120                 125

Ser Lys Glu Gly Phe Leu Lys Tyr Leu Val Asp Ser Lys Leu Val Phe
    130                 135                 140

Asp Thr Ile Glu Arg Ile Val Asp Glu Ser Glu Asn Val Ser Tyr Ala
145                 150                 155                 160

Tyr Phe Arg Arg Thr Gly Leu Glu Arg Cys Glu Ser Ile Glu Lys Asp
                165                 170                 175

Leu Gln Trp Leu Arg Glu Gln Asp Leu Val Ile Pro Gly Pro Ser Asn
            180                 185                 190

Val Gly Val Ser Tyr Ala Lys Tyr Leu Glu Glu Gln Ala Gly Glu Ser
        195                 200                 205

Ala Pro Leu Phe Leu Ser His Phe Tyr Ser Ile Tyr Phe Ser His Ile
    210                 215                 220
```

```
Ala Gly Gly Gln Val Leu Val Arg Gln Val Ser Glu Lys Leu Leu Glu
225                 230                 235                 240

Gly Lys Glu Leu Glu Phe Asn Arg Trp Glu Gly Asp Ala Gln Asp Leu
                245                 250                 255

Leu Lys Gly Val Arg Glu Lys Leu Asn Val Leu Gly Glu His Trp Ser
            260                 265                 270

Arg Asp Glu Lys Asn Lys Cys Leu Lys Glu Thr Ala Lys Ala Phe Lys
        275                 280                 285

Tyr Met Gly Gln Ile Val Arg Leu Ile Ile Leu
    290                 295

<210> SEQ ID NO 17
<211> LENGTH: 282
<212> TYPE: PRT
<213> ORGANISM: Arabidopsis thaliana

<400> SEQUENCE: 17

Met Ala Tyr Leu Ala Pro Ile Ser Ser Ser Leu Ser Ile Phe Lys Asn
1               5                   10                  15

Pro Gln Leu Ser Arg Phe Gln Phe Ser Ser Ser Ser Pro Asn Pro Leu
            20                  25                  30

Phe Leu Arg Pro Arg Ile Gln Ile Leu Ser Met Thr Met Asn Lys Ser
        35                  40                  45

Pro Ser Leu Val Val Val Ala Thr Thr Ala Ala Glu Lys Gln Lys
    50                  55                  60

Lys Arg Tyr Pro Gly Glu Ser Lys Gly Phe Val Glu Glu Met Arg Phe
65                  70                  75                  80

Val Ala Met Arg Leu His Thr Lys Asp Gln Ala Lys Glu Gly Glu Lys
                85                  90                  95

Glu Thr Lys Ser Ile Glu Glu Arg Pro Val Ala Lys Trp Glu Pro Thr
            100                 105                 110

Val Glu Gly Tyr Leu Arg Phe Leu Val Asp Ser Lys Leu Val Tyr Asp
        115                 120                 125

Thr Leu Glu Leu Ile Ile Gln Asp Ser Asn Phe Pro Thr Tyr Ala Glu
130                 135                 140

Phe Lys Asn Thr Gly Leu Glu Arg Ala Glu Lys Leu Ser Thr Asp Leu
145                 150                 155                 160

Glu Trp Phe Lys Glu Gln Gly Tyr Glu Ile Pro Glu Pro Thr Ala Pro
                165                 170                 175

Gly Lys Thr Tyr Ser Gln Tyr Leu Lys Glu Leu Ala Glu Lys Asp Pro
            180                 185                 190

Gln Ala Phe Ile Cys His Phe Tyr Asn Ile Tyr Phe Ala His Ser Ala
        195                 200                 205

Gly Gly Arg Met Ile Gly Arg Lys Val Ala Glu Arg Ile Leu Asp Asn
    210                 215                 220

Lys Glu Leu Glu Phe Tyr Lys Trp Asp Gly Glu Leu Ser Gln Leu Leu
225                 230                 235                 240

Gln Asn Val Arg Glu Lys Leu Asn Lys Val Ala Glu Glu Trp Thr Arg
                245                 250                 255

Glu Glu Lys Asn His Cys Leu Glu Glu Thr Glu Lys Ser Phe Lys Tyr
            260                 265                 270

Ser Gly Glu Ile Leu Arg Leu Ile Leu Ser
        275                 280
```

<210> SEQ ID NO 18
<211> LENGTH: 276
<212> TYPE: PRT
<213> ORGANISM: Arabidopsis thaliana

<400> SEQUENCE: 18

Met Ile Ala Ala Gly Ala Lys Ser Leu Gly Leu Ser Met Ala Ser
1               5                   10                  15

Pro Lys Gly Ile Phe Asp Ser Asn Ser Met Ser Asn Ser Arg Ser Val
                20                  25                  30

Val Val Val Arg Ala Cys Val Ser Met Asp Gly Ser Gln Thr Leu Ser
            35                  40                  45

His Asn Lys Asn Gly Ser Ile Pro Glu Val Lys Ser Ile Asn Gly His
    50                  55                  60

Thr Gly Gln Lys Gln Gly Pro Leu Ser Thr Val Gly Asn Ser Thr Asn
65                  70                  75                  80

Ile Lys Trp His Glu Cys Ser Val Glu Lys Val Asp Arg Gln Arg Leu
                85                  90                  95

Leu Asp Gln Lys Gly Cys Val Ile Trp Val Thr Gly Leu Ser Gly Ser
                100                 105                 110

Gly Lys Ser Thr Leu Ala Cys Ala Leu Asn Gln Met Leu Tyr Gln Lys
            115                 120                 125

Gly Lys Leu Cys Tyr Ile Leu Asp Gly Asp Asn Val Arg His Gly Leu
    130                 135                 140

Asn Arg Asp Leu Ser Phe Lys Ala Glu Asp Arg Ala Glu Asn Ile Arg
145                 150                 155                 160

Arg Val Gly Glu Val Ala Lys Leu Phe Ala Asp Ala Gly Ile Ile Cys
                165                 170                 175

Ile Ala Ser Leu Ile Ser Pro Tyr Arg Thr Asp Arg Asp Ala Cys Arg
                180                 185                 190

Ser Leu Leu Pro Glu Gly Asp Phe Val Glu Val Phe Met Asp Val Pro
            195                 200                 205

Leu Ser Val Cys Glu Ala Arg Asp Pro Lys Gly Leu Tyr Lys Leu Ala
    210                 215                 220

Arg Ala Gly Lys Ile Lys Gly Phe Thr Gly Ile Asp Asp Pro Tyr Glu
225                 230                 235                 240

Pro Pro Leu Asn Cys Glu Ile Ser Leu Gly Arg Glu Gly Gly Thr Ser
                245                 250                 255

Pro Ile Glu Met Ala Glu Lys Val Val Gly Tyr Leu Asp Asn Lys Gly
                260                 265                 270

Tyr Leu Gln Ala
    275

<210> SEQ ID NO 19
<211> LENGTH: 571
<212> TYPE: PRT
<213> ORGANISM: Zea mays

<400> SEQUENCE: 19

Met Asp Thr Gly Cys Leu Ser Ser Met Asn Ile Thr Gly Ala Ser Gln
1               5                   10                  15

Thr Arg Ser Phe Ala Gly Gln Leu Pro Pro Gln Arg Cys Phe Ala Ser
                20                  25                  30

Ser His Tyr Thr Ser Phe Ala Val Lys Lys Leu Val Ser Arg Asn Lys
            35                  40                  45

Gly Arg Arg Ser His Arg Arg His Pro Ala Leu Gln Val Val Cys Lys

```
                50                  55                  60
Asp Phe Pro Arg Pro Leu Glu Ser Thr Ile Asn Tyr Leu Glu Ala
 65                  70                  75                  80

Gly Gln Leu Ser Ser Phe Phe Arg Asn Ser Glu Arg Pro Ser Lys Pro
                 85                  90                  95

Leu Gln Val Val Val Ala Gly Ala Gly Leu Ala Gly Leu Ser Thr Ala
                100                 105                 110

Lys Tyr Leu Ala Asp Ala Gly His Lys Pro Ile Leu Leu Glu Ala Arg
                115                 120                 125

Asp Val Leu Gly Gly Lys Val Ala Ala Trp Lys Asp Glu Asp Gly Asp
            130                 135                 140

Trp Tyr Glu Thr Gly Leu His Ile Phe Phe Gly Ala Tyr Pro Asn Ile
145                 150                 155                 160

Gln Asn Leu Phe Gly Glu Leu Arg Ile Glu Asp Arg Leu Gln Trp Lys
                165                 170                 175

Glu His Ser Met Ile Phe Ala Met Pro Asn Lys Pro Gly Glu Phe Ser
            180                 185                 190

Arg Phe Asp Phe Pro Glu Thr Leu Pro Ala Pro Ile Asn Gly Ile Trp
            195                 200                 205

Ala Ile Leu Arg Asn Asn Glu Met Leu Thr Trp Pro Glu Lys Val Lys
210                 215                 220

Phe Ala Ile Gly Leu Leu Pro Ala Met Val Gly Gly Gln Pro Tyr Val
225                 230                 235                 240

Glu Ala Gln Asp Gly Leu Thr Val Ser Glu Trp Met Lys Lys Gln Gly
                245                 250                 255

Val Pro Asp Arg Val Asn Asp Glu Val Phe Ile Ala Met Ser Lys Ala
            260                 265                 270

Leu Asn Phe Ile Asn Pro Asp Glu Leu Ser Met Gln Cys Ile Leu Ile
            275                 280                 285

Ala Leu Asn Arg Phe Leu Gln Glu Lys His Gly Ser Lys Met Ala Phe
            290                 295                 300

Leu Asp Gly Asn Pro Pro Glu Arg Leu Cys Met Pro Ile Val Asp His
305                 310                 315                 320

Ile Arg Ser Arg Gly Gly Glu Val Arg Leu Asn Ser Arg Ile Lys Lys
                325                 330                 335

Ile Glu Leu Asn Pro Asp Gly Thr Val Lys His Phe Ala Leu Ser Asp
                340                 345                 350

Gly Thr Gln Ile Thr Gly Asp Ala Tyr Val Cys Ala Thr Pro Val Asp
                355                 360                 365

Ile Phe Lys Leu Leu Val Pro Gln Glu Trp Ser Glu Ile Thr Tyr Phe
                370                 375                 380

Lys Lys Leu Glu Lys Leu Val Gly Val Pro Val Ile Asn Val His Ile
385                 390                 395                 400

Trp Phe Asp Arg Lys Leu Asn Asn Thr Tyr Asp His Leu Leu Phe Ser
                405                 410                 415

Arg Ser Ser Leu Leu Ser Val Tyr Ala Asp Met Ser Val Thr Cys Lys
                420                 425                 430

Glu Tyr Tyr Asp Pro Asn Arg Ser Met Leu Glu Leu Val Phe Ala Pro
                435                 440                 445

Ala Asp Glu Trp Ile Gly Arg Ser Asp Thr Glu Ile Ile Asp Ala Thr
            450                 455                 460

Met Glu Glu Leu Ala Lys Leu Phe Pro Asp Glu Ile Ala Ala Asp Gln
465                 470                 475                 480
```

Ser Lys Ala Lys Ile Leu Lys Tyr His Ile Val Lys Thr Pro Arg Ser
            485                 490                 495

Val Tyr Lys Thr Val Pro Asn Cys Glu Pro Cys Arg Pro Leu Gln Arg
                500                 505                 510

Ser Pro Ile Glu Gly Phe Tyr Leu Ala Gly Asp Tyr Thr Lys Gln Lys
            515                 520                 525

Tyr Leu Ala Ser Met Glu Gly Ala Val Leu Ser Gly Lys Leu Cys Ala
        530                 535                 540

Gln Ser Ile Val Gln Asp Tyr Ser Arg Leu Ala Leu Arg Ser Gln Lys
545                 550                 555                 560

Ser Leu Gln Ser Gly Glu Val Pro Val Pro Ser
            565                 570

<210> SEQ ID NO 20
<211> LENGTH: 266
<212> TYPE: PRT
<213> ORGANISM: Panax ginseng

<400> SEQUENCE: 20

Met Ala Ala Ser Thr Met Ala Leu Ser Ser Pro Ser Phe Ala Gly Met
1               5                   10                  15

Ala Val Lys Val Ala Pro Ser Ser Glu Leu Phe Gly Ser Gly Arg
            20                  25                  30

Ile Ser Met Arg Lys Thr Gly Lys Pro Ala Ala Ser Ser Gly Ser
        35                  40                  45

Pro Trp Tyr Gly Pro Asp Arg Val Lys Tyr Leu Gly Pro Phe Ser Gly
50                  55                  60

Glu Ala Pro Ser Tyr Leu Thr Gly Glu Phe Pro Gly Asp Tyr Gly Trp
65                  70                  75                  80

Asp Thr Ala Gly Leu Ser Ala Asp Pro Glu Thr Phe Ala Lys Asn Arg
            85                  90                  95

Glu Leu Glu Val Ile His Ser Arg Trp Ala Met Leu Gly Ala Leu Gly
            100                 105                 110

Cys Val Phe Pro Glu Leu Leu Ala Arg Asn Gly Val Lys Phe Gly Glu
            115                 120                 125

Ala Val Trp Phe Lys Ala Gly Ser Gln Ile Phe Ser Glu Gly Gly Leu
        130                 135                 140

Asp Tyr Leu Gly Asn Pro Ser Leu Val His Ala Gln Ser Ile Leu Ala
145                 150                 155                 160

Ile Trp Ala Thr Gln Val Ile Leu Met Gly Ala Val Glu Gly Tyr Arg
                165                 170                 175

Ile Ala Gly Gly Pro Leu Gly Glu Val Val Asp Pro Leu Tyr Pro Gly
            180                 185                 190

Gly Ser Phe Asp Pro Leu Gly Leu Ala Glu Asp Pro Glu Ala Phe Ala
        195                 200                 205

Glu Leu Lys Val Lys Glu Leu Lys Asn Gly Arg Leu Ala Met Phe Ser
        210                 215                 220

Met Phe Gly Phe Phe Val Gln Ala Ile Val Thr Gly Lys Gly Pro Leu
225                 230                 235                 240

Glu Asn Leu Ala Asp Pro Leu Ala Asp Pro Val Asn Asn Asn Ala Trp
                245                 250                 255

Ala Tyr Ala Thr Asn Phe Val Pro Gly Lys
            260                 265

```
<210> SEQ ID NO 21
<211> LENGTH: 126
<212> TYPE: PRT
<213> ORGANISM: Chlamydomonas reinhardtii

<400> SEQUENCE: 21

Met Ala Met Ala Met Arg Ser Thr Phe Ala Ala Arg Val Gly Ala Lys
1               5                   10                  15

Pro Ala Val Arg Gly Ala Arg Pro Ala Ser Arg Met Ser Cys Met Ala
            20                  25                  30

Tyr Lys Val Thr Leu Lys Thr Pro Ser Gly Asp Lys Thr Ile Glu Cys
        35                  40                  45

Pro Ala Asp Thr Tyr Ile Leu Asp Ala Ala Glu Glu Ala Gly Leu Asp
    50                  55                  60

Leu Pro Tyr Ser Cys Arg Ala Gly Ala Cys Ser Ser Cys Ala Gly Lys
65                  70                  75                  80

Val Ala Ala Gly Thr Val Asp Gln Ser Asp Gln Ser Phe Leu Asp Asp
                85                  90                  95

Ala Gln Met Gly Asn Gly Phe Val Leu Thr Cys Val Ala Tyr Pro Thr
            100                 105                 110

Ser Asp Cys Thr Ile Gln Thr His Gln Glu Glu Ala Leu Tyr
        115                 120                 125

<210> SEQ ID NO 22
<211> LENGTH: 148
<212> TYPE: PRT
<213> ORGANISM: Chlamydomonas reinhardtii

<400> SEQUENCE: 22

Met Leu Gln Leu Ala Asn Arg Ser Val Arg Ala Lys Ala Ala Arg Ala
1               5                   10                  15

Ser Gln Ser Ala Arg Ser Val Ser Cys Ala Ala Lys Arg Gly Ala
            20                  25                  30

Asp Val Ala Pro Leu Thr Ser Ala Leu Ala Val Thr Ala Ser Ile Leu
        35                  40                  45

Leu Thr Thr Gly Ala Ala Ser Ala Ser Ala Ala Asp Leu Ala Leu Gly
    50                  55                  60

Ala Gln Val Phe Asn Gly Asn Cys Ala Ala Cys His Met Gly Gly Arg
65                  70                  75                  80

Asn Ser Val Met Pro Glu Lys Thr Leu Asp Lys Ala Ala Leu Glu Gln
                85                  90                  95

Tyr Leu Asp Gly Gly Phe Lys Val Glu Ser Ile Ile Tyr Gln Val Glu
            100                 105                 110

Asn Gly Lys Gly Ala Met Pro Ala Trp Ala Asp Arg Leu Ser Glu Glu
        115                 120                 125

Glu Ile Gln Ala Val Ala Glu Tyr Val Phe Lys Gln Ala Thr Asp Ala
    130                 135                 140

Ala Trp Lys Tyr
145

<210> SEQ ID NO 23
<211> LENGTH: 317
<212> TYPE: PRT
<213> ORGANISM: Chlamydomonas reinhardtii

<400> SEQUENCE: 23

Met Ser Asn Gln Val Phe Thr Thr Leu Arg Ala Ala Thr Leu Ala Val
1               5                   10                  15
```

```
Ile Leu Gly Met Ala Gly Leu Ala Val Ser Pro Ala Gln Ala Tyr
             20                  25                  30

Pro Val Phe Ala Gln Gln Asn Tyr Ala Asn Pro Arg Glu Ala Asn Gly
             35                  40                  45

Arg Ile Val Cys Ala Asn Cys His Leu Ala Gln Lys Ala Val Glu Ile
 50                      55                  60

Glu Val Pro Gln Ala Val Leu Pro Asp Thr Val Phe Glu Ala Val Ile
 65                  70                  75                  80

Glu Leu Pro Tyr Asp Lys Gln Val Lys Gln Val Leu Ala Asn Gly Lys
                 85                  90                  95

Lys Gly Asp Leu Asn Val Gly Met Val Leu Ile Leu Pro Glu Gly Phe
            100                 105                 110

Glu Leu Ala Pro Pro Asp Arg Val Pro Ala Glu Ile Lys Glu Lys Val
            115                 120                 125

Gly Asn Leu Tyr Tyr Gln Pro Tyr Ser Pro Glu Gln Lys Asn Ile Leu
130                 135                 140

Val Val Gly Pro Val Pro Gly Lys Lys Tyr Ser Glu Met Val Val Pro
145                 150                 155                 160

Ile Leu Ser Pro Asp Pro Ala Lys Asn Lys Asn Val Ser Tyr Leu Lys
                165                 170                 175

Tyr Pro Ile Tyr Phe Gly Gly Asn Arg Gly Arg Gly Gln Val Tyr Pro
            180                 185                 190

Asp Gly Lys Lys Ser Asn Asn Thr Ile Tyr Asn Ala Ser Ala Ala Gly
            195                 200                 205

Lys Ile Val Ala Ile Thr Ala Leu Ser Glu Lys Lys Gly Gly Phe Glu
210                 215                 220

Val Ser Ile Glu Lys Ala Asn Gly Glu Val Val Asp Lys Ile Pro
225                 230                 235                 240

Ala Gly Pro Asp Leu Ile Val Lys Glu Gly Gln Thr Val Gln Ala Asp
                245                 250                 255

Gln Pro Leu Thr Asn Asn Pro Asn Val Gly Gly Phe Gly Gln Ala Glu
            260                 265                 270

Thr Glu Ile Val Leu Gln Asn Pro Ala Arg Ile Gln Gly Leu Leu Val
            275                 280                 285

Phe Phe Ser Phe Val Leu Leu Thr Gln Val Leu Leu Val Leu Lys Lys
290                 295                 300

Lys Gln Phe Glu Lys Val Gln Leu Ala Glu Met Asn Phe
305                 310                 315

<210> SEQ ID NO 24
<211> LENGTH: 211
<212> TYPE: PRT
<213> ORGANISM: Oryza sativa

<400> SEQUENCE: 24

Met Gln Ala Ile Leu Ala Ala Met Ala Ala Gln Thr Leu Leu Phe
 1               5                  10                  15

Ser Ala Thr Ala Pro Pro Ala Ser Leu Phe Gln Ser Pro Ser Ser Ala
             20                  25                  30

Arg Pro Phe His Ser Leu Arg Leu Ala Ala Gly Pro Gly Ala Ala
             35                  40                  45

Ala Ala Arg Ala Leu Val Val Ala Asp Ala Thr Lys Lys Ala Val Ala
 50                      55                  60

Val Leu Lys Gly Thr Ser Gln Val Glu Gly Val Val Thr Leu Thr Gln
```

```
                65                  70                  75                  80
Asp Asp Gln Gly Pro Thr Thr Val Asn Val Arg Val Thr Gly Leu Thr
                    85                  90                  95

Pro Gly Leu His Gly Phe His Leu His Glu Phe Gly Asp Thr Thr Asn
                100                 105                 110

Gly Cys Ile Ser Thr Gly Pro His Phe Asn Pro Asn Asn Leu Thr His
                115                 120                 125

Gly Ala Pro Glu Asp Glu Val Arg His Ala Gly Asp Leu Gly Asn Ile
            130                 135                 140

Val Ala Asn Ala Glu Gly Val Ala Glu Ala Thr Ile Val Asp Lys Gln
145                 150                 155                 160

Ile Pro Leu Ser Gly Pro Asn Ser Val Val Gly Arg Ala Phe Val Val
                165                 170                 175

His Glu Leu Glu Asp Asp Leu Gly Lys Gly Gly His Glu Leu Ser Leu
                180                 185                 190

Ser Thr Gly Asn Ala Gly Gly Arg Leu Ala Cys Gly Val Val Gly Leu
                195                 200                 205

Thr Pro Leu
    210

<210> SEQ ID NO 25
<211> LENGTH: 430
<212> TYPE: PRT
<213> ORGANISM: Arabidopsis thaliana

<400> SEQUENCE: 25

Met Ala Ala Thr Thr Asn Ser Phe Leu Val Gly Ser Asn Asn Thr Gln
1               5                   10                  15

Ile Pro Ala Leu Lys Pro Lys Ser Ser Gln Ser Phe Leu His Leu
            20                  25                  30

Ser Lys Pro Asn Thr Val Asn Phe Val Ser Lys Thr Lys Pro Val Ala
            35                  40                  45

Val Arg Cys Val Ala Ser Thr Thr Gln Val Gln Asp Gly Val Arg Ser
50                  55                  60

Gly Ser Val Gly Ser Gln Glu Arg Val Phe Asn Phe Ala Ala Gly Pro
65                  70                  75                  80

Ala Thr Leu Pro Glu Asn Val Leu Leu Lys Ala Gln Ala Asp Leu Tyr
                85                  90                  95

Asn Trp Arg Gly Ser Gly Met Ser Val Met Glu Met Ser His Arg Gly
                100                 105                 110

Lys Glu Phe Leu Ser Ile Ile Gln Lys Ala Glu Ser Asp Leu Arg Gln
            115                 120                 125

Leu Leu Glu Ile Pro Gln Glu Tyr Ser Val Leu Phe Leu Gln Gly Gly
            130                 135                 140

Ala Thr Thr Gln Phe Ala Ala Leu Pro Leu Asn Leu Cys Lys Ser Asp
145                 150                 155                 160

Asp Thr Val Asp Phe Val Val Thr Gly Ser Trp Gly Asp Lys Ala Val
                165                 170                 175

Lys Glu Ala Lys Lys Tyr Cys Lys Thr Asn Val Ile Trp Ser Gly Lys
                180                 185                 190

Ser Glu Lys Tyr Thr Lys Val Pro Ser Phe Glu Glu Leu Glu Gln Thr
            195                 200                 205

Pro Asp Ala Lys Tyr Leu His Ile Cys Ala Asn Glu Thr Ile His Gly
    210                 215                 220
```

Val Glu Phe Lys Asp Tyr Pro Val Pro Lys Asn Gly Phe Leu Val Ala
225                 230                 235                 240

Asp Met Ser Ser Asn Phe Cys Ser Lys Pro Val Asp Val Ser Lys Phe
            245                 250                 255

Gly Val Ile Tyr Gly Gly Ala Gln Lys Asn Val Gly Pro Ser Gly Val
        260                 265                 270

Thr Ile Val Ile Ile Arg Lys Asp Leu Ile Gly Asn Ala Gln Asp Ile
    275                 280                 285

Thr Pro Val Met Leu Asp Tyr Lys Ile His Asp Glu Asn Ser Ser Leu
290                 295                 300

Tyr Asn Thr Pro Pro Cys Phe Gly Ile Tyr Met Cys Gly Leu Val Phe
305                 310                 315                 320

Glu Asp Leu Leu Glu Gln Gly Gly Leu Lys Glu Val Glu Lys Lys Asn
            325                 330                 335

Gln Arg Lys Ala Asp Leu Leu Tyr Asn Ala Ile Glu Ser Asn Gly
        340                 345                 350

Phe Phe Arg Cys Pro Val Glu Lys Ser Val Arg Ser Leu Met Asn Val
    355                 360                 365

Pro Phe Thr Leu Glu Lys Ser Glu Leu Glu Ala Glu Phe Ile Lys Glu
370                 375                 380

Ala Ala Lys Glu Lys Met Val Gln Leu Lys Gly His Arg Ser Val Gly
385                 390                 395                 400

Gly Met Arg Ala Ser Ile Tyr Asn Ala Met Pro Leu Ala Gly Val Glu
            405                 410                 415

Lys Leu Val Ala Phe Met Lys Asp Phe Gln Ala Lys His Ala
        420                 425                 430

<210> SEQ ID NO 26
<211> LENGTH: 993
<212> TYPE: PRT
<213> ORGANISM: Arabidopsis thaliana

<400> SEQUENCE: 26

Met Ala Ser Ala Ala Ala Ser Pro Ser Leu Ser Leu Asn Pro Thr
1               5                   10                  15

Ser His Phe Gln His Gln Thr Ser Leu Val Thr Trp Leu Lys Pro Pro
            20                  25                  30

Pro Ser Ser Ala Leu Phe Arg Arg Lys Thr Leu Pro Phe Phe Glu Arg
        35                  40                  45

His Ser Leu Pro Ile Ser Ala Ser Ser Ser Ser Ser Ser Ser Ser
    50                  55                  60

Thr Ser Leu Ser Val His Glu Lys Pro Ile Ser Asn Ser Val His Phe
65                  70                  75                  80

His Gly Asn Leu Ile Glu Ser Phe Glu Asn Gln Asp Ser Ser Tyr Ala
            85                  90                  95

Gly Thr Ile Lys Gly Ala Ser Leu Ile Glu Glu Leu Glu Asn Pro Val
        100                 105                 110

Glu Arg Asn Gly Leu Ser Gly Arg Arg Leu Phe Met Gln Asp Pro
    115                 120                 125

Pro Trp Ile Ser Ala Leu Phe Leu Lys Gly Leu Ser Lys Met Val Asp
130                 135                 140

Gln Thr Leu Lys Ile Glu Arg Lys Asp Ile Asp Lys Arg Lys Phe Asp
145                 150                 155                 160

Ser Leu Arg Arg Arg Gln Val Lys Glu Glu Thr Glu Ala Trp Glu Arg
            165                 170                 175

```
Met Val Asp Glu Tyr Arg Asp Leu Glu Lys Glu Met Cys Glu Lys Asn
            180                 185                 190

Leu Ala Pro Asn Leu Pro Tyr Val Lys His Met Phe Leu Gly Trp Phe
        195                 200                 205

Gln Pro Leu Lys Asp Val Ile Glu Arg Glu Gln Lys Leu Gln Lys Asn
    210                 215                 220

Lys Ser Lys Lys Val Arg Ala Ala Tyr Ala Pro His Ile Glu Leu Leu
225                 230                 235                 240

Pro Ala Asp Lys Met Ala Val Ile Val Met His Lys Met Met Gly Leu
                245                 250                 255

Val Met Ser Gly His Glu Asp Gly Cys Ile Gln Val Val Gln Ala Ala
            260                 265                 270

Val Ser Ile Gly Ile Ala Ile Glu Gln Glu Val Arg Ile His Asn Phe
        275                 280                 285

Leu Lys Arg Thr Arg Lys Asn Asn Ala Gly Asp Ser Gln Glu Glu Leu
    290                 295                 300

Lys Glu Lys Gln Leu Leu Arg Lys Arg Val Asn Ser Leu Ile Arg Arg
305                 310                 315                 320

Lys Arg Ile Ile Asp Ala Leu Lys Val Val Lys Ser Glu Gly Thr Lys
                325                 330                 335

Pro Trp Gly Arg Ala Thr Gln Ala Lys Leu Gly Ser Arg Leu Leu Glu
            340                 345                 350

Leu Leu Ile Glu Ala Ala Tyr Val Gln Pro Pro Leu Thr Gln Ser Gly
        355                 360                 365

Asp Ser Ile Pro Glu Phe Arg Pro Ala Phe Arg His Arg Phe Lys Thr
    370                 375                 380

Val Thr Lys Tyr Pro Gly Ser Lys Leu Val Arg Arg Tyr Gly Val Ile
385                 390                 395                 400

Glu Cys Asp Ser Leu Leu Ala Gly Leu Asp Lys Ser Ala Lys His
                405                 410                 415

Met Leu Ile Pro Tyr Val Pro Met Leu Val Pro Pro Lys Arg Trp Lys
                420                 425                 430

Gly Tyr Asp Lys Gly Gly Tyr Leu Phe Leu Pro Ser Tyr Ile Met Arg
            435                 440                 445

Thr His Gly Ser Lys Lys Gln Gln Asp Ala Leu Lys Asp Ile Ser His
    450                 455                 460

Lys Thr Ala His Arg Val Phe Glu Ala Leu Asp Thr Leu Gly Asn Thr
465                 470                 475                 480

Lys Trp Arg Val Asn Arg Asn Ile Leu Asp Val Val Glu Arg Leu Trp
                485                 490                 495

Ala Asp Gly Gly Asn Ile Ala Gly Leu Val Asn Arg Gly Asp Val Pro
            500                 505                 510

Ile Pro Glu Lys Pro Ser Ser Glu Asp Pro Glu Glu Leu Gln Ser Trp
        515                 520                 525

Lys Trp Ser Ala Arg Lys Ala Asn Lys Ile Asn Arg Glu Arg His Ser
    530                 535                 540

Leu Arg Cys Asp Val Glu Leu Lys Leu Ser Val Ala Arg Lys Met Lys
545                 550                 555                 560

Asp Glu Glu Gly Phe Tyr Tyr Pro His Asn Leu Asp Phe Arg Gly Arg
                565                 570                 575

Ala Tyr Pro Met His Pro His Leu Asn His Leu Ser Ser Asp Leu Cys
            580                 585                 590
```

```
Arg Gly Thr Leu Glu Phe Ala Glu Gly Arg Pro Leu Gly Lys Ser Gly
            595                 600                 605

Leu His Trp Leu Lys Ile His Leu Ala Asn Leu Tyr Ala Gly Gly Val
    610                 615                 620

Glu Lys Leu Ser His Asp Ala Arg Leu Ala Phe Val Glu Asn His Leu
625                 630                 635                 640

Asp Asp Ile Met Asp Ser Ala Glu Asn Pro Ile His Gly Lys Arg Trp
                645                 650                 655

Trp Leu Lys Ala Glu Asp Pro Phe Gln Cys Leu Ala Ala Cys Val Ile
            660                 665                 670

Leu Thr Gln Ala Leu Lys Ser Pro Ser Pro Tyr Ser Val Ile Ser His
        675                 680                 685

Leu Pro Ile His Gln Asp Gly Ser Cys Asn Gly Leu Gln His Tyr Ala
    690                 695                 700

Ala Leu Gly Arg Asp Ser Phe Glu Ala Ala Val Asn Leu Val Ala
705                 710                 715                 720

Gly Glu Lys Pro Ala Asp Val Tyr Ser Glu Ile Ser Arg Arg Val His
                725                 730                 735

Glu Ile Met Lys Lys Asp Ser Ser Lys Asp Pro Glu Ser Asn Pro Thr
            740                 745                 750

Ala Ala Leu Ala Lys Ile Leu Ile Thr Gln Val Asp Arg Lys Leu Val
        755                 760                 765

Lys Gln Thr Val Met Thr Ser Val Tyr Gly Val Thr Tyr Val Gly Ala
    770                 775                 780

Arg Glu Gln Ile Lys Arg Arg Leu Glu Glu Lys Gly Val Ile Thr Asp
785                 790                 795                 800

Glu Arg Met Leu Phe Ala Ala Ala Cys Tyr Ser Ala Lys Val Thr Leu
                805                 810                 815

Ala Ala Leu Gly Glu Ile Phe Glu Ala Ala Arg Ala Ile Met Ser Trp
            820                 825                 830

Leu Gly Asp Cys Ala Lys Ile Ile Ala Ser Asp Asn His Pro Val Arg
        835                 840                 845

Trp Ile Thr Pro Leu Gly Leu Pro Val Val Gln Pro Tyr Cys Arg Ser
    850                 855                 860

Glu Arg His Leu Ile Arg Thr Ser Leu Gln Val Leu Ala Leu Gln Arg
865                 870                 875                 880

Glu Gly Asn Thr Val Asp Val Arg Lys Gln Arg Thr Ala Phe Pro Pro
                885                 890                 895

Asn Phe Val His Ser Leu Asp Gly Thr His Met Met Met Thr Ala Val
            900                 905                 910

Ala Cys Arg Glu Ala Gly Leu Asn Phe Ala Gly Val His Asp Ser Tyr
        915                 920                 925

Trp Thr His Ala Cys Asp Val Asp Thr Met Asn Arg Ile Leu Arg Glu
    930                 935                 940

Lys Phe Val Glu Leu Tyr Asn Thr Pro Ile Leu Glu Asp Leu Leu Gln
945                 950                 955                 960

Ser Phe Gln Glu Ser Tyr Pro Asn Leu Val Phe Pro Pro Val Pro Lys
                965                 970                 975

Arg Gly Asp Phe Asp Leu Lys Glu Val Leu Lys Ser Gln Tyr Phe Phe
            980                 985                 990

Asn

<210> SEQ ID NO 27
```

```
<211> LENGTH: 293
<212> TYPE: PRT
<213> ORGANISM: Spinacia oleracea

<400> SEQUENCE: 27

Met Ala Thr Ser Thr Ser Ser Ser Leu Ser Leu Ser Phe Phe Ser Ser
1               5                   10                  15

Ser Leu Phe Ser Ser Lys Ser Arg Asn Phe Ser Ser Lys Pro Ile Leu
            20                  25                  30

Lys Leu Pro Ser Ser Ser His Ser Gln Thr Ser Leu Ser Leu Ser Ile
            35                  40                  45

Lys Ser Glu Leu Ile Pro Leu Pro Ile Leu Asn Phe Ser Gly Glu Lys
50                      55                  60

Val Gly Glu Thr Phe Leu Asn Leu Lys Thr Ala Pro Pro Glu Lys Ala
65                  70                  75                  80

Arg Ala Val Val His Arg Gly Leu Ile Thr His Leu Gln Asn Lys Arg
                85                  90                  95

Arg Gly Thr Ala Ser Thr Leu Thr Arg Ala Glu Val Arg Gly Gly Gly
            100                 105                 110

Arg Lys Pro Tyr Pro Gln Lys Lys Thr Gly Arg Ala Arg Arg Gly Ser
            115                 120                 125

Gln Gly Ser Pro Leu Arg Pro Gly Gly Gly Val Ile Phe Gly Pro Lys
    130                 135                 140

Pro Arg Asp Trp Thr Ile Lys Met Asn Lys Lys Glu Arg Arg Leu Ala
145                 150                 155                 160

Leu Ser Thr Ala Ile Ala Ser Ala Val Gly Asn Ser Phe Val Val Glu
                165                 170                 175

Glu Phe Ala Glu Asn Phe Glu Lys Pro Lys Thr Lys Asp Phe Ile Ala
            180                 185                 190

Ala Met Gln Arg Trp Gly Leu Asp Pro Ala Glu Lys Ser Leu Phe Phe
            195                 200                 205

Leu Met Asp Leu Val Glu Asn Val Glu Lys Ser Gly Arg Asn Ile Arg
        210                 215                 220

Thr Leu Lys Leu Leu Thr Pro Arg Ser Leu Asn Leu Phe Asp Val Leu
225                 230                 235                 240

Asn Ala Glu Lys Leu Val Phe Thr Glu Gly Thr Ile Gln Tyr Leu Asn
            245                 250                 255

Gln Arg Tyr Gly Val Asp Thr Leu Glu Asp Glu Asp Glu Glu Glu Glu
            260                 265                 270

Glu Glu Glu Glu Gly Glu Glu Val Asp Asp Gly Val Glu Asp Gly Thr
        275                 280                 285

Pro Glu Pro Ala Glu
    290
```